(12) United States Patent
Omori

(10) Patent No.: US 7,308,452 B2
(45) Date of Patent: Dec. 11, 2007

(54) METHOD AND DEVICE FOR RECORDING SEQUENCE INFORMATION ON BIOLOGICAL COMPOUNDS

(76) Inventor: Satoshi Omori, 11-7-627 Nishibori 4-chome, Saitama-shi, Saitama (JP) 338-0832

( * ) Notice: Subject to any disclaimer, the term of this patent is extended or adjusted under 35 U.S.C. 154(b) by 520 days.

(21) Appl. No.: 10/689,395

(22) Filed: Oct. 20, 2003

(65) Prior Publication Data
US 2005/0004920 A1    Jan. 6, 2005

Related U.S. Application Data

(63) Continuation-in-part of application No. PCT/JP02/03801, filed on Apr. 17, 2002.

(30) Foreign Application Priority Data

Apr. 18, 2001 (JP) .............................. 2001-120335
Nov. 30, 2001 (JP) .............................. 2001-368002

(51) Int. Cl.
    G06F 17/00    (2006.01)
(52) U.S. Cl. .................................... 707/100; 707/104.1
(58) Field of Classification Search ................ 707/100, 707/104.1, 3, 10; 702/19, 20
    See application file for complete search history.

(56) References Cited

FOREIGN PATENT DOCUMENTS

| JP | 3-63876 | 3/1991 |
|---|---|---|
| JP | 4-54656 | 2/1992 |
| JP | 5-143472 | 6/1993 |
| JP | 6-162096 | 6/1994 |
| JP | 6-348760 | 12/1994 |
| JP | 8-255176 | 1/1996 |
| JP | 8-320834 | 12/1996 |

OTHER PUBLICATIONS

Compression of Nucleotide Databases for Fast Searching Comput. Appl. Oct. 1997 vol. 13, No. 5.*
Finire fields and Galois fields http://mathworld.wolfram.com/FiniteField.html Jun. 15, 2000.*

* cited by examiner

Primary Examiner—Hosain Alam
Assistant Examiner—Leon J. Harper
(74) Attorney, Agent, or Firm—Jordan and Hamburg LLP

(57) ABSTRACT

A method and device for recording sequence information on biological compounds such as nucleotides and amino acids in as small amounts of data as possible are provided. The text data representing the sequence of a series of nucleotides constituting the DNA of the standard sample E is converted into binary data using a conversion table, and the binary data is divided into plural m-bit partial data ($A(i,j)$) arranged in plural columns and rows ($m \geq 16$). Then a first set of parities ($B1(i) \sim B3(i)$) are computed by applying an operation of Galois field $GF(2^m)$ to the partial data ($A(i,j)$) of each column and a second set of parities ($C1(j) \sim C3(j)$) are computed by applying an operation of Galois field $GF(2^m)$ to the partial data ($A(i,j)$) of each row. The sequence of the nucleotides is represented approximately by the parity information.

2 Claims, 14 Drawing Sheets

FIG. 7

STANDARD SAMPLE E

| j \ i | 1 | 2 | 3 | 4 |
|---|---|---|---|---|
| 1 | AGCTTTTCATTCTGAC | TGCAACGGGCAATATG | TCTCTGTGTGGATTAA | AAAAAGAGTGTCTGAT |
| 2 | AGCAGCTTCTGAACTG | GTTACCTGCCGTGAGT | AAATTAAAATTTTATT | GACTTAGGTCACTAAA |
| 3 | TACTTTAACCAATATA | GGCATAGCGCACAGAC | AGATAAAAATTACAGA | GTACACAACATCCATG |
| 4 | AAACGCATTAGCACCA | CCATTACCACCACCAT | CACCATTACCACAGGT | AACGGTGCGCGGCTGAC |
| 5 | GCGTACAGGAAACACA | GAAAAAGCCCGCACC | TGACAGTGCGGGCTTT | TTTTTCGACCAAAGG |
| 6 | TAACGAGGTAACAACC | ATGCGAGTGTTGAAGT | TCGGCCGGTACATCAGT | GGCAAATGCAGAACGT |
| 7 | TTTCTGCGTGTGCCG | ATATTCTGAAAAGCAA | TGGCCAGGCAGGGCAG | GTGGCCACCCGTCCT |
| 8 | CTGCCCCCGCCAAAAT | CACCAACCACCTGGTG | GCGATGATTGAAAAAA | CCATTAGCGCGGCAGGA |
| 9 | TGCTTTACCCAATATC | AGCGATGCCGAACGTA | TTTTTGCCGAACTTT | GACGGGGACTCGCCGCC |
| 10 | GCCCAGCCGGGGTTCC | CGCTGGCGCAATTGAA | AACTTCGTCGATCAG | GAATTGCCCAAATAA |
| 11 | AACATGTCCTGCATGG | CATTAGTTTGTTGGGG | CAGTGCCCGGATAGCA | TCAACGCTGCGCTGAT |
| 12 | TTGCCCGTGCGAGAAA | ATGTCGATCGCCATTA | TGGCCGGCGTATTAGA | AGCGCGCAATCTACCGTCG |
| 13 | GTTACTGTTATCGATC | CGGTCGAAAACTGCT | GGCAGTGGGGCATTAC | CTCGAATCTACCGTCG |
| 14 | ATATTGCTGAGTCCAC | CCCGGTATTGCGGCA | AGCCCGCATTCCGGCTG | ATCACATGGTGCTGAT |
| 15 | GGCAGGTTTCACGCCG | GGTAATGAAAAGGGC | AACTGGTGGTGCTTGG | ACGCAACGGTTCCGAC |
| 16 | TACTCTGCCTGCGGTG | TGCCTGCCTGTTTACG | CGCCGATTGTTGCGAG | ATTGGACGGACGTTG |
| 17 | ACGGGGTCTATACCTG | CGACCCGCGTCAGGTG | CCCGATGCGACGTGT | TGAAGTCCATGTCCTA |
| 18 | CCAGGAAGCGATGGAG | CTTTCCTACTTGCGGCG | CTAAAGTTCTTCACCC | CCGCACCATTACCCCC |
| 19 | ATCGCCCAGTTCCAGA | TCCCTTGCTGATTAA | AAATACCGGAAATCCT | CAAGCACCAGCTACGC |
| 20 | TCATTGGTGCCACCCG | TGATGAAGACGAATTA | CCGGTCAAGGCATT | CCAATCTGAATAACAT |
| 21 | GGCAATGTTCAGCCGTT | TCTGGTCCGGGATGA | AAGGGATGGTCGGCAA | GGCGGCGGAATACAGCA |
| 22 | GCAGCGATGTCACGCG | CCCGTATTCCGTGGT | GCTGATTACGAACGGG | TCTTCCGGAAGAGTTCTA |
| 23 | TCAGTTTCTGCCGTCC | ACAAAGCGACTGTGTG | TGAGCTGAACGGGCAA | TGCAGGAATACGGGCTGG |
| 24 | CCTGGAACTGGTGGTA | GGCTTACTGGAGCCGC | TGGCAGTGACGGGAAATTC | GCTGGCCACTGGCCC |
| 25 | GTGGTAGGTGATGGTA | TGCGCACCTTGCTCAG | GATCTTCGGCGAATTGG | TTTGCCGCACTGGTGGT |
| 26 | GCGCCAATATCAACAT | TGTCGGCCATTGGCTG | GGATTCATCAGATGCT | CAATCTCTCTGTCGTGGT |
| 27 | AAATAACGATGATGCG | ACCACTGGCGTGACCG | TTACTCATCAGATGT | GTTCAATACCGATCAG |
| 28 | GTTATCGAAGTGTTTG | TGATTGGCGTCGGTGG | CGTTGGCGTCGGTGG | CTGGAGCAACTCGAAGC |
| 29 | GTCAGCCAAAGCTGGCT | GAAGAATAAACATATC | GACTTACGTTGCTGCC | GTGTTGCCAACTCGAA |
| 30 | GGCTCTGCTCACCAAT | GTACATGCCCTTAATCG | TGGAAAACTGAAACAATT | AGAACTGCTGAACCGG |
| 31 | AAAGAGCCGTTTAATC | TCGGGCGCTTAATTCG | CCTCGTGAAACAATAT | CATCTGCTGAACCGG |
| 32 | TCATTGTTGACTGCAC | TTCCAGCAGGCAGTG | GCGATCAATAATGCCG | ACTTCCTGCCGGAAGG |

$$A(3, 11) = asc(T(3, 11))$$
$$= asc(CAGTGCCCGGATAGCA) = hex(41434754154414747434347544747443)$$

DIFFERENCES BETWEEN STANDARD SAMPLE E AND SAMPLE F

| j \ i | 1 | 2 | 3 | 4 | C1F(i) | C2F(i) | C3F(i) |
|---|---|---|---|---|---|---|---|
| 1–15 | | | | | | | |
| 16 | | X1=hex(43475447474343754<br>43475443544434154)<br>→chr(X1)=TACTCTGCTGCGGTGC<br>=TF(1,16) | | X2=hex(47545447434147747<br>4341474754545441)<br>→chr(X2)=ATTTGGACGGACGTTG<br>=TF(4,16) | C1F(16) | C2F(16) | C3F(16) |
| 17 | | Y1=hex(47544343415441544<br>43544747474341)<br>→chr(Y1)=ACGGGTCTATACCTG<br>=TF(1,17) | | Y2=hex(41544343544475441<br>4743544741414754)<br>→chr(Y2)=TGAAGTCGATGTCCTA<br>=TF(4,17) | C1F(17) | C2F(17) | C3F(17) |
| 18–32 | | | | | | | |
| B1F(i) | B1F(1) | | | B1F(4) | | | |
| B2F(i) | B2F(1) | | | B2F(4) | | | |
| B3F(i) | B3F(1) | | | B3F(4) | | | |

FIG. 12

CALCULATION OF X1, X2, Y1, Y2 (GF($2^{128}$)) —141

| | |
|---|---|
| X1 +AF(2,16) +AF(3,16) +X2 =C1(16) | ··· (G1) |
| AF(1,16) +AF(2,16) +AF(3,16) +AF(4,16) =C1F(16) | ··· (G2) |

—142

| | |
|---|---|
| X1 + $\alpha$ · AF(2,16) + $\alpha^2$ · AF(3,16) + $\alpha^3$ · X2 =C2(16) | ··· (G3) |
| AF(1,16) + $\alpha$ · AF(2,16) + $\alpha^2$ · AF(3,16) + $\alpha^3$ · AF(4,16) =C2F(16) | ··· (G4) |

—143

| | |
|---|---|
| X1+X2 =C1(16) -C1F(16) +AF(1,16) +AF(4,16) =C1X | ··· (G5) |
| X1+ $\alpha^3$ · X2=C2(16) -C2F(16) +AF(1,16) + $\alpha^3$ · AF(4,16) =C2X | ··· (G6) |

—144

$$X1 = \frac{\begin{vmatrix} C1X & 1 \\ C2X & \alpha^3 \end{vmatrix}}{\begin{vmatrix} 1 & 1 \\ 1 & \alpha^3 \end{vmatrix}}, \quad X2 = \frac{\begin{vmatrix} 1 & C1X \\ 1 & C2X \end{vmatrix}}{\begin{vmatrix} 1 & 1 \\ 1 & \alpha^3 \end{vmatrix}} \quad \cdots (G7)$$

—145

| | |
|---|---|
| Y1+Y2 =C1(17) -C1F(17) +AF(1,17) +AF(4,17) =C1Y | ··· (G8) |
| Y1+ $\alpha^3$ · Y2=C2(17) -C2F(17) +AF(1,17) + $\alpha^3$ · AF(4,17) =C2Y | ··· (G9) |

—146

$$Y1 = \frac{\begin{vmatrix} C1Y & 1 \\ C2Y & \alpha^3 \end{vmatrix}}{\begin{vmatrix} 1 & 1 \\ 1 & \alpha^3 \end{vmatrix}}, \quad Y2 = \frac{\begin{vmatrix} 1 & C1Y \\ 1 & C2Y \end{vmatrix}}{\begin{vmatrix} 1 & 1 \\ 1 & \alpha^3 \end{vmatrix}} \quad \cdots (G10)$$

END

F I G. 1 3

STANDARD SAMPLE E

| i \ j | 1 | 2 | 3 | 4 | 5 |
|---|---|---|---|---|---|
| 1 | 1bfe3ed2d82560cd | eeddd4f00011ded3 | 186fb42d7cada747 | 03c03fcf4bc5e2c0 | cbf0a0cc58c66212 |
| 2 | 13003c8472208e8d | 0263c628a3ca28a3 | 8a3ca21709765d2 | 672140884001a98a | d21d95bfff192805 |
| 3 | c245c20a36477d07 | e59723875800d8427 | fed9df6933ed4060 | da16156175a29ebb | b6aa68038a0a2b5d |
| 4 | 64d3d000a3c65a14 | dbf2a0ce1936909c | ffda42ff4952e69a | 6a1a55fa9b5983d0 | 0bf9e4e143f6a030 |
| 5 | 08deb6358f1fdf55 | 876a5318e09b66d3 | f69d644037939a3c | d69673c419997882 | 7cb7ce4e979002db |
| 6 | 58758f2b90eca79 | 33db47a2a69cf658 | 1a63e96d388d76d3 | 585fe29a5c340059 | 0b5d76f526097e92 |
| 7 | cbb6d976d6dadfc9 | 9a4f7d913f52527d | 255eccad92a6785d | a93645f7d07937ac | a14l9351bfacbe59 |
| 8 | b01fbe2aa628f2aa | 39a87e84eaf6b4f0 | 032940eb818a1726 | e3d76869d341243c | a5e0563fa0ed0c23 |
| 9 | 5837e19fed7a5534 | 054d79635966667bf | 6193789a9cfe9d7 | e3d76869d341243c | e1fed9fa20192ddd |
| 10 | 91b42560d85047ec | ad42d0105bcb51a6 | d61d250996d68f3b9 | 75c5d35cd98af675 | 4ee5903efda62d6a |
| 11 | 6683823de68f6e1 | 53bed09b83bb79d7 | 030934d928b59d99 | f2e384db7e0ca4e1 | 7ce41dfdd3d67975 |
| 12 | 9f59766db5182d06 | 78601b5b410c08ce | 4bc9ded977da0b90 | 5bb6e2837235af0e | d402d61410b5981a |
| 13 | 011a7f0ee566f0f9 | ae7404338edb42a5 | e3df4b62fa1a161d | 653833692fad9905 | 0000000000000000 |
| B1B(i) |  |  |  |  |  |
| B2B(i) |  |  |  |  |  |
| B3B(i) |  |  |  |  |  |

| | SAMPLE G | | | TG(i, j) |
|---|---|---|---|---|
| i | 1 | 2 | 3 | 4 |
| j | | | | |
| 1 | MRVLKFGG | TSVANAER | FLRVADIL | ESNARQGQ |
| 2 | VATVLSAP | AKITNHLV | AMIEKTIS | GQDALPNI |
| 3 | SDAERIFA | ELLTGLAA | AQPGFPLA | QLKTFVDQ |
| 4 | EFAQIKHV | LHGISLLG | QCPDSINA | ALICRGEK |
| 5 | MSIAIMAG | VLEARGHN | VTVIDPVE | KLLAVGHY |
| 6 | LESTVDIA | ESTRRIAA | SRIPADHM | VLMAGFTA |
| 7 | GNEKGELV | VLGRNGSD | YSAAVLAA | CLRADCCE |
| 8 | IWTDVDGV | YTCDPRQV | PDARLLKS | MSYQEAME |
| 9 | LSYFGAKV | LHPRTITP | IAQFQIPC | LIKNTGNP |
| 10 | QAPGTLIG | ASRDEDEL | PVKGISNL | NNMAMFSV |
| 11 | SGPGMKGM | VGMAARVF | AAMSRARI | SVVLITQS |
| 12 | SSEYSISF | CVPQSDCV | RAERAMQE | EFYLELKE |
| 13 | GLLEPLAV | TERLAIIS | VVGDGMRT | LRGISAKF |
| 14 | FAALARAN | INIVAIAQ | GSSERSIS | VVVNNDDA |
| 15 | TTGVRVTH | QMLFNTDQ | VIEVFVIG | VGGVGGAL |
| 16 | LEQLKRQQ | SWLKNKHI | DLRVCGVA | NSKALLTN |
| 17 | VHGLNLEN | WQEELAQA | KEPFNLGR | LIRLVKEY |
| 18 | HLLNPVIV | DCTSSQAV | ADQYADFL | REGFHVVT |
| 19 | PNKKANTS | SMDYYHQL | RYAAEKSR | RKFLYDTN |
| 20 | VGAGLPVI | ENLQNLLN | AGDELMKF | SGILSGSL |
| 21 | SYIFGKLD | EGMSFSEA | TTLAREMG | YTEPDPRD |
| 22 | DLSGMDVA | RKLLILAR | ETGRELEL | ADIEIEPV |
| 23 | LPAEFNAE | GDVAAFMA | NLSQLDDL | FAARVAKA |
| 24 | RDEGKVLR | YVGNIDED | GVCRVKIA | EVDGNDPL |
| 25 | FKVKNGEN | ALAFYSHY | YQPLPLVL | RGYGAGND |
| 26 | VTAAGVFA | DLLRTLSW | KLGV0000 | 00000000 |

(0=hex(00))

AG(3, 11) = asc(TG(3, 11))
= asc(AAMSRARI) = hex(495241152534d4141)

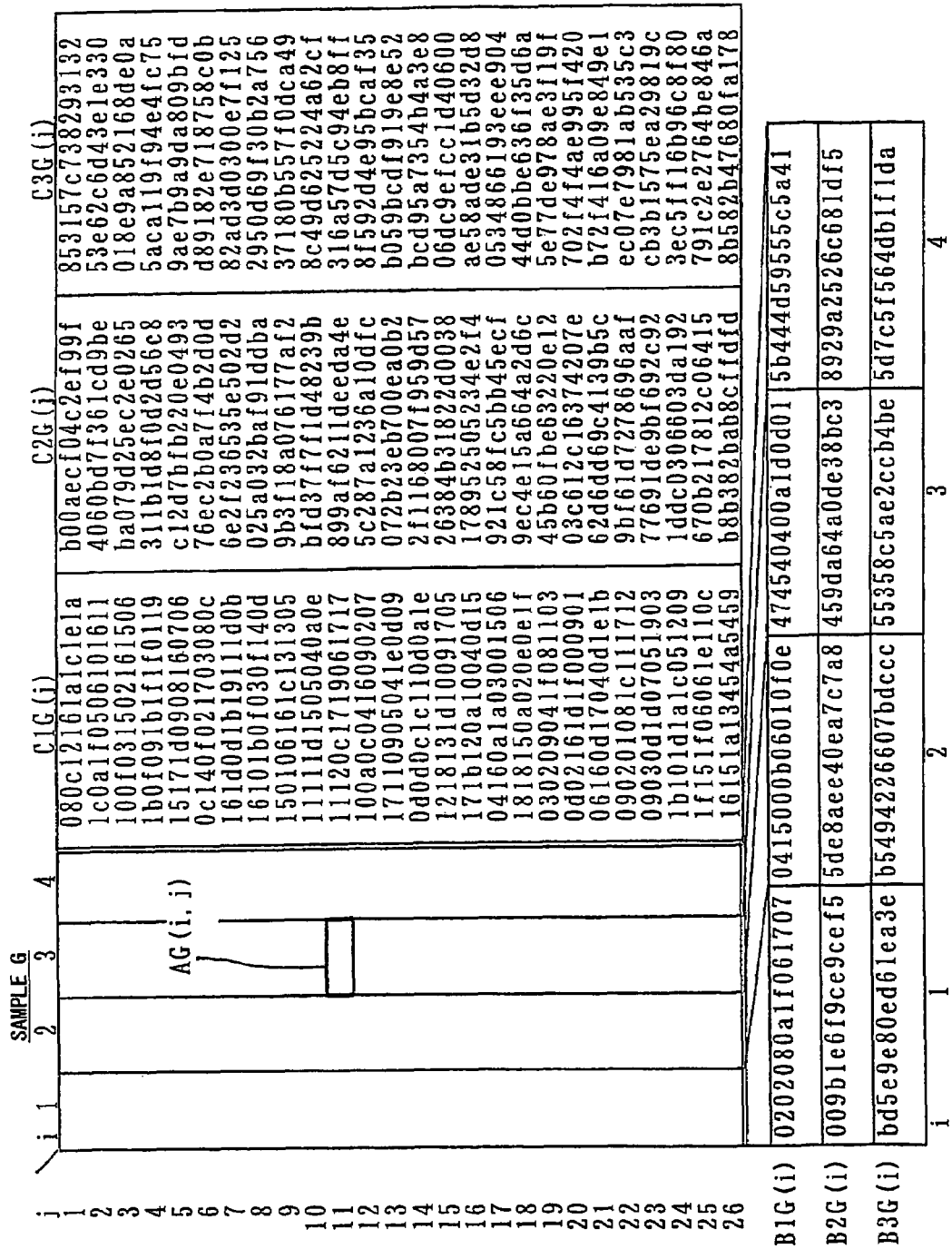

METHOD AND DEVICE FOR RECORDING SEQUENCE INFORMATION ON BIOLOGICAL COMPOUNDS

CROSS REFERENCE TO RELATED APPLICATIONS

The present application is a continuation-in-part of PCT Application No. PCT/JP02/03801 filed Apr. 17, 2002, which application has not been published in English under PCT Article 21(2), and both the present application and the preceding PCT application claim priority under 35 U.S.C. § 119 to Japanese patent application JP2001-120335 filed Apr. 18, 2001, and Japanese patent application JP2001-368002 filed Nov. 30, 2001. Moreover, all the disclosures including descriptions, claims, drawings, and abstracts of the Japanese patent application JP2001-120335 filed Apr. 18, 2001, the Japanese patent application JP2001-368002 filed Nov. 30, 2001, and U.S. application Ser. No. 10/272,107 filed Oct. 16, 2002 are incorporated herein by reference.

TECHNICAL FIELD

The invention relates to a method and device for recording sequence information on biological compounds such as a set of nucleotides constituting at least part of nucleic acids, e.g. DNA (deoxyribonucleic acid), RNA (ribonucleic acid), and genes, and a set of amino acids constituting at least part of proteins.

The invention further relates to a method for supplying sequence information suitable for a business model to supply the sequence information and to a computer-readable medium in which the sequence information is recorded.

BACKGROUND ART

The sequences of nucleotides (or bases) in pairs of polymer strands constituting the DNA molecules of humans and other organisms (animals, plants, microorganisms, etc.) are being deciphered worldwide. In order to record the deciphered nucleotide sequences, four kinds of nucleotides which constitute DNA are expressed in four different one-byte (eight-bit) text data by allocating the character A, G, C, or T for the nucleotide including adenine, guanine, cytosine, or thymine respectively as the nitrogenous base. Consequently, sequence information on DNA which consists of two polymer strands with each strand comprising n (n is an integer) nucleotides is represented in n-byte text data by expressing each nucleotide of one strand one by one as the corresponding character selected from the four characters A, G, C, and T (or a, g, c, and t). Similarly, the sequence of n nucleotides constituting an RNA molecule is recorded in n-byte text data by allocating the character A, G, C, or U (or a, g, c, or u) for the nucleotide including adenine, guanine, cytosine, or uracil respectively.

In the case of humans, since each chain of the DNA molecules in the first or largest chromosome and in the 22nd or smallest one is a sequence of nearly 250,000,000 and 50,000,000 nucleotides respectively, the nucleotide sequence of the DNA in each chromosome can be expressed in about 250-50 MB text data. In addition, since the human genome (all DNA information) is expressed as the sequence of nearly 3,000,000,000 nucleotides, it is recorded in about 3 GB text data. For practical uses, the original text data may be recorded or transmitted as a compressed file of about half the size of the original data by applying the conventional file compression techniques.

Following the decipherment of nucleotide sequences of DNA, the functions of the proteins synthesized according to the genes in DNA are widely researched. In these researches, the sequence of a protein molecule which consists of n amino acids is represented by n-byte text data since each of 20 kinds of amino acids constituting protein molecules is expressed as the text data of three characters (for example, Ala, Cys, Glu, etc.) in three-Letter Code or one character (for example, A, C, E, etc.) in one-Letter Code. As ordinary proteins consist of the sequence of nearly 20 to 1000 amino acids, each of the sequences of those proteins may be recorded in about 1 KB text data, at the most. Moreover, it is estimated that there are nearly 30,000 human genes in total and there may be nearly 100,000 kinds of protein molecules including theoretical ones.

As described above, in order to record the human genome in the form of text data, about 3 GB of memory is necessary. Even if the conventional file compression techniques are employed, nearly 1 GB of memory may be needed. Recently, DNA sequences of living organisms other than humans such as colon bacilli and various viruses are also disclosed to the public. If these DNA sequences are collected in text data, we may need several hundred MB of memory for each of those organisms. Such is the case in recording sequence information on RNA.

Thus, when information on DNA sequences of humans or other organisms is recorded in the form of text files or the conventional compressed files, the recording medium with huge memory capacity such as a DVD-ROM disk capable of recording nearly 5 GB data is necessary. There is additionally an inconvenience that both the time needed for reading sequence information from the recording medium and the time needed for processing sequence information are long.

Moreover, since the transmission rate of the current general communications network is about 5 Mbps, when we transmit information on DNA sequences of the size of, for example, 1 GB via the communications network, the transmission time will be around thirty minutes. Especially recently the digital cellular phone system is being widespread as a communications medium. It may however be difficult to use it to transmit at least the DNA sequence information of humans since the transmission rate of the present cellular phone system is as low as nearly 1 Mbps.

There is also a problem of how to assure that the nucleotide sequences, which are assumed to be equal and held by two or more researchers as a standard sequence, are really equal. This happens, for example, when genes in the DNA of a certain microorganism are studied by the researchers. That is, it is not necessarily easy for two or more researchers to mutually verify in a short time that their text data expressing the nucleotide sequence of the DNA are completely equal when each of their text data has several MB data (data for several million characters).

In this connection, as a use of information on DNA sequences of humans or other organisms, we can think of a task to search the difference between a standard DNA sequence and a sample DNA sequence. Such a task will be needed when the SNP (Single Nucleotide Polymorphism) is searched. However, there is an inconvenience that a relatively long time is needed to compare the two text data and search the difference between them when both text data represent the huge nucleotide sequence of DNA.

Furthermore, a new business has started in which several suppliers offer many pieces of information on DNA sequences to users such as researchers of the pharmaceutical companies. In the business it is preferable for the suppliers to avoid offering overlapping information to the users. It is thus convenient for the users to be able to check easily whether the nucleotide sequences of DNA offered by the plural suppliers are equal or not without disclosing the entire information on the nucleotide sequences to the public. In addition, when the suppliers offer the users the DNA information through, for example, a communications network, a business model is needed in which necessary information can be transmitted to the users in as less data as possible so as to shorten the transmission time. Moreover, it is preferable that the users can easily check whether the offered DNA information contains transmission errors, etc. The above-mentioned problems are included similarly in treating information on nucleotide sequences of RNA.

In addition, the amino acid sequence of a protein is recorded by the text data of about 1 KB at the most and there are about 100,000 kinds of proteins including theoretical ones. Thus, if we express sequence information on all kinds of proteins in the form of text data, we will have a large amount of data. Accordingly, it is preferable to record the sequence of each protein in as less data as possible and we need a system by which we can easily verify whether two pieces of sequence information on proteins are equal.

It is therefore an object of the present invention to provide a method and device for recording approximate small amounts of data of sequence information on biological compounds such as a set of nucleotides of nucleic acids or a set of amino acids of proteins.

It is a second object of the invention to provide a method and device for detecting the difference between two pieces of sequence information on biological compounds by a small amount of data and, if necessary, recovering the difference.

It is a third object of the invention to provide a business model (or a method for supplying information) for making a user easily verify whether the user's data and the supplier's original data are equal and detect the difference between them using a small amount of data when supplying sequence information on biological compounds such as a set of nucleotides or a set of amino acids to the user.

It is a fourth object of the invention to provide a computer-readable medium in which approximate information on sequences of biological compounds is recorded with a small amount of data.

DISCLOSURE OF INVENTION

According to one aspect of the invention, a first method for recording sequence information on biological compounds comprises the following steps:

dividing the text data representing the sequence of the biological compounds or the numerical data obtained by converting the text data based on a conversion rule into plural m-bit partial data (A(i,j)) arranged in plural columns in the arranged direction corresponding to the direction along which the biological compounds are placed and in plural rows in the non-arranged direction which crosses the arranged direction, where m is an integer larger than or equal to 16;

computing a first set of parity information (B1(i), B2(i), B3(i)) by applying a first operation of Galois field $GF(2^m)$ along the non-arranged direction to a set of the partial data of each column;

computing a second set of parity information (C1(j), C2(j), C3(j)) by applying a second operation of Galois field $GF(2^m)$ along the arranged direction to a set of the partial data of each row; and representing the sequence information on the biological compounds by the first and second sets of parity information.

In this aspect of the invention, the biological compounds are supposed to be, for example, a series of nucleotides or a series of amino acids. The series of nucleotides are, for example, at least part of one chain of a pair of polymer chains constituting DNA (deoxyribonucleic acid), at least part of the polymer chain constituting RNA (ribonucleic acid), or at least part of a gene. The sequence of the series of nucleotide can be considered as the sequence of bases each of which is included in each nucleotide. On the other hand, the series of amino acids are at least part of the sequence of amino acids constituting a certain protein, for example.

Provided that the entire number of the biological compounds is NT and each biological compound is expressed in one character (e. g. one alphabet letter) of ASCII code (ANSI form) or Unicode, the size of the total text data corresponding to the sequence of the biological compounds becomes NT bytes or 2 NT bytes, respectively. In this estimation, the codes such as space, numerals, return, etc., which are used to make the sequence easy to read, are left out. Then, in the case of FIG. 7, for example, the text data is divided into plural partial text data T(i,j) arranged in N columns (i=1 to N) in the arranged direction and in M rows (j=1 to M) in the non-arranged direction. Each of the partial text data T(i,j) is then converted into m-bit partial data A(i,j) as shown in FIG. 8. Each of the m-bit partial data A(i,j) represents the sequence of n (n=16 in the case of FIG. 8) consecutive biological compounds.

In this case, the simplest way of expressing the partial data A(i,j) is to use the partial text data T(i,j) itself that can be considered as numerical data. That is, when the text data is recorded in ASCII codes, the ASCII codes can be used as the partial data A(i,j). When the text data is recorded in Unicode, the codes in which each character is expressed in the upper one-byte code of the corresponding two-byte Unicode may be used as the partial data A(i,j). However, it is preferable that the partial text data T(i,j) is converted to a numerical data block by using a conversion table (a predetermined rule) in which each character representing a biological compound is converted to numerical data with six bits or less, for example, and the numerical data block is considered as the partial data A(i,j) in order to reduce the amount of data to be processed.

Next, plural pieces of data approximately representing the sequence information on each column and each row are computed by performing operations to each of the m-bit partial data A(i,j) in the non-arranged direction and the arranged direction, respectively. For the computation we need a field in which addition, subtraction, multiplication, and division of m-bit data can be performed. In a first method of the present invention Galois field (extension Galois field) $GF(2^m)$ is used as the field. One advantage of using Galois field $GF(2^m)$ is that the sequence information can be recorded concisely in small amounts of data, because when a piece of information is obtained by performing predetermined operations (the first and second operations) of addition, subtraction, multiplication, and division to the m-bit partial data A(i,j) of each column and each row respectively and, if necessary, m-bit coefficients, the size of the piece of information (which is referred to as "parity information" in the present invention) is m bits.

Provided that the field represented by numbers modulo 2 (i.e. 0 and 1) is denoted by $Z_2$, the operations on Galois field $GF(2^m)$ can be defined by using an irreducible polynomial GF(X) of m-th degree with coefficients defined on the field $Z_2$. That is, suppose that two m-bit partial data $A(i,j)$ and $A(i',j')$ are expressed as numbers $(a_{m-1}\ a_{m-2}\ \ldots\ a_1\ a_0)$ and $(b_{m-1}\ b_{m-2}\ \ldots\ b_1\ b_0)$ ($a_k$ and $b_k$ are 0 or 1) respectively in binary notation, then these numbers are converted to the following polynomials AF(X) and BF(X) whose degree is lower than or equal to (m−1):

$$AF(X) = a_{m-1} \cdot X^{m-1} + a_{m-2} \cdot X^{m-2} + \ldots + a_1 \cdot X + a_0, \quad (1)$$

$$BF(X) = b_{m-1} \cdot X^{m-1} + b_{m-2} \cdot X^{m-2} + \ldots + b_1 \cdot X + b_0. \quad (2)$$

In this case, in order to add AF(X) and BF(X) together on Galois field $GF(2^m)$, we have only to add the coefficients $a_k$ and $b_k$ of each degree k (k=0 to (m−1)) together on the field $Z_2$. Addition and subtraction yield the same result on the field $Z_2$. Consequently, the coefficients expressed in binary notation of the resultant polynomial are the result in vector representation obtained by adding the partial data $A(i,j)$ and $A(i',j')$ together on Galois field $GF(2^m)$. This is the same result as is obtained by performing a bit-wise exclusive-OR operation to the two coefficients of each degree.

Then, in order to multiply AF(X) by BF(X) on Galois field $GF(2^m)$, the product is computed first by performing ordinary multiplication, and a polynomial CF(X) is obtained as the remainder ($c_k$ is 0 or 1) by dividing the product by the irreducible polynomial GF(X) as follows. This operation is called the multiplication modulo the irreducible polynomial GF(X). In this calculation, addition (subtraction) of the coefficients of each degree of X is performed on the field $Z_2$.

$$CF(X) = c_{m-1} \cdot X^{m-1} + c_{m-2} \cdot X^{m-2} + \ldots + c_1 \cdot X + c_0 \quad (3)$$

The coefficients $(c_{m-1}\ c_{m-2}\ \ldots\ c_1\ c_0)$ in binary notation of the polynomial CF(X) are the result obtained by multiplying the partial data $A(i,j)$ by the partial data $A(i',j')$ on Galois field $GF(2^m)$. Moreover, suppose that an arbitrary m-bit coefficient is β, then the coefficient β is expressed as a polynomial DF(X) whose degree is less than or equal to (m−1) similar to equation (2). Therefore, in order to multiply the partial data $A(i,j)$ by the coefficient β, we have only to compute the product of the polynomial AF(X) of equation (1) and the polynomial DF(X) modulo the irreducible polynomial GF(X). Furthermore, in order to divide the partial data $A(i,j)$ by the coefficient β, for example, we have only to multiply the partial data $A(i,j)$ by the inverse element $β^{-1}$ of β.

Therefore, all m-bit data (which include all partial data $A(i,j)$) can be considered as the elements of Galois field $GF(2^m)$ in vector representation, and all m-bit data can be expressed in the polynomials similar to equation (1) whose degree is less than or equal to (m−1) in polynomial representation. Moreover, when a set of m-bit data in vector representation are converted to a series of characters using the inverted relation of the conversion table (a predetermined rule) which allocates the partial data $A(i,j)$ to biological compounds (a string of characters), the series of biological compounds corresponding to the data are obtained.

According to this aspect of the invention, for example, as shown in FIG. 8, the plural partial data $A(i,j)$ are arranged in N columns (i=1 to N) in the arranged direction and in M rows (j=1 to M) in the non-arranged direction, and a first set of parity information (B1(i), B2(i), B3(i)) are obtained for each column and a second set of parity information (C1(j), C2(j), C3(j)) are obtained for each row. Each piece of parity information (for example, B1(1)) of these two sets of parity information is represented by m-bit data as well as one partial data $A(i,j)$.

In this case, the amount of data DT1 of all the partial data $A(i,j)$ is as follows:

$$DT1 = m \cdot N \cdot M \text{(bits)}. \quad (4)$$

In addition, provided that each of the first and second sets of parity information includes e pieces of parity information (e is an integer larger than or equal to one), the amount of data DS1 of all the parity information is as follows. Here, when e pieces of parity information are included, up to e partial data $A(i,j)$ can be recovered for each column and each row, respectively.

$$DS1 = m \cdot e \cdot (N+M) \text{(bits)} \quad (5)$$

Therefore, if it is assumed that the biological compounds are nucleotides constituting DNA and N=64, M=128, and e=2, the amount of data DT1 and DS1 are as follows from equations (4) and (5):

$$DT1 = m \cdot 8192 \text{(bits)}, \quad (6)$$

$$DS1 = m \cdot 384 \text{(bits)} \approx DT1/20. \quad (7)$$

The amount of data of the parity information is therefore reduced to almost 1/20 of that of all the partial data $A(i,j)$. In this method, because the sequence of the DNA in each chromosome of humans is expressed as the text data of nearly 50-250 MB, if the text data is divided into 500-2500 blocks and two sets of parity information are computed for each block, the amount of data of all the parity information will be reduced to nearly 1/20 of that of the text data, i.e. nearly from 2.5 MB to 12.5 MB quantity. Moreover, if the quantity of the partial data $A(i,j)$ is 1/f of that of the text data, for example, the quantity of the parity information will be reduced to 1/f of the above estimation.

According to this aspect of the invention, the information (the parity information) expressing the original sequence information of the biological compounds approximately can be recorded in a file with less data than that of the original text data. Such a small amount of data can be recorded in the mediums with small memory capacity, which can be easily played by ordinary computers, such as a CD-ROM and flash-ROM besides the mediums with large memory capacity such as a DVD-ROM. And since a small amount of data can be transmitted in a short time via a communications network, the parity information can be offered to users at low prices via cellular phone systems, for example.

Then users can identify the differences between two sequences of biological compounds easily using the first and second sets of parity information. In addition, provided that the number of the differences in each column or row is less than or equal to e, the sequence corresponding to the differences can be recovered by using the parity information.

Furthermore, as the file in which text data is recorded can be compressed by using conventional compression techniques (ZIP file, LHA file, etc.), the file in which the parity information of the invention is recorded can be compressed by using conventional compression techniques. However, it is very useful to reduce the size of the original file, for when a compressed file is used, it must be decompressed to its original file.

Then, in the first method for recording sequence information, when it is assumed that a is a primitive element of Galois field $GF(2^m)$, for example, the first set of parity information includes the sum of plural products obtained by multiplying a set of the partial data $(A(i,j))$ of each column along the non-arranged direction by $\alpha^{sp}$, $\alpha^{s(p+1)}$, $\alpha^{s(p+2)}$, ..., $\alpha^{s(p+dp)}$, where s and p are nonnegative integers and dp is an integer lager than or equal to one; and the second set of parity information includes the sum of plural products obtained by multiplying a set of the partial data (A(i,j)) of each row along the arranged direction by $\alpha^{tq}$, $\alpha^{t(q+1)}$, $\alpha^{t(q+2)}$, ..., $\alpha^{t(q+dq)}$, where t and q are nonnegative integers and dq is an integer lager than or equal to one.

In this case, assuming that p=q=0, the first set of parity information B1(i) and the second set of parity information C1(j) can be computed respectively by the following operations on Galois field $GF(2^m)$. The $\Sigma$ of equation (8) denotes the summation over the range 1 to M of j, and the $\Sigma$ of equation (9) denotes the summation over the range 1 to N of i.

$$B1(i)=\Sigma\alpha^{s(j-1)} \cdot A(i,j)=A(i,1)+ \alpha^s \cdot A(i,2)+\alpha^{2s} \cdot A(1,3)+\ldots+\alpha^{(M-1)s} \cdot A(i,M) \quad (8)$$

$$C1(j)=\Sigma\alpha^{t(i-1)} \cdot A(i,j)=A(1,j)+\alpha^t \cdot A(2,j)+ \alpha^{2t} \cdot A(3,j)+\ldots+\alpha^{(N-1)t} \cdot A(N,j) \quad (9)$$

Then, assuming that s=t=0 in equations (8) and (9), each of the parity information B1(i) and C1(j) reduces to the sum of the partial data A(i,j) on Galois field $GF(2^m)$, that is, the value obtained by performing the exclusive-OR operation to the partial data A(i,j) of each column or row, respectively. Thus, the approximative information on the sequences of each column and each row is obtained by performing simple operations. However, in this case, if two partial data A(i,j) are exchanged in each column or each row, the value of the parity information B1(i) or C1(j) remains the same, respectively.

Then, assuming that s=t=1, the parity information B1(i) or C1(j) is the sum of the products obtained by multiplying the partial data A(i,j) of each column or row, respectively, by 1, $\alpha$, $\alpha^2$, $\alpha^3$, .... In this case, if two partial data A(i,j) are exchanged in each column or each row, the value of the parity information B1(i) or C1(j) varies, respectively. As a result, the differences between two sequences of biological compounds, for example, can be identified more precisely. And, in order to multiply two partial data in each column or each row by mutually different coefficients using a certain s ($\neq 0$) (or t ($\neq 0$)), the coefficients $\alpha^{s(j-1)}$ (or $\alpha^{t(i-1)}$) should differ from each other. For this, provided that a is a primitive element of Galois field $GF(2^m)$, we have only to assume that the number of the partial data A(i,j) of each column or each row is less than or equal to $(2^m-1)/s$ (or $(2^m-1)/t$). That is, the size of the sequence of biological compounds to be treated will be the largest by assuming that $\alpha$ is a primitive element.

When two sequences of biological compounds are compared, one partial data A(i,j) that differs from the counterpart in each column and each row is recovered correctly using one piece of parity information in each column and each row, respectively. Accordingly, for example, the SNP (Single Nucleotide Polymorphism) of genes can be easily detected and the normal sequence corresponding to it can be easily recovered.

Furthermore, in order to recover s' and t' partial data A(i,j) differing from the counterparts in each column and each row (s' and t' are integers larger than or equal to two), respectively, the first set of parity information (B1(i), B2(i), B3(i)) should include s' sums computed for mutually different values of the integer s for each of the plural columns and the second set of parity information (C1(j), C2(j), C3(j)) should include t' sums computed for mutually different values of t for each on the plural rows. In order to recover the partial data differing from the counterparts, we have only to solve simultaneous first-degree equations with s' (t') unknown numbers on Galois field $GF(2^m)$.

Moreover, in this aspect of the invention, the number of the second set of parity information may be made smaller than the number of the first set of parity information by making the number of the partial data placed in the arranged direction smaller than the number of the partial data placed in the non-arranged direction.

Especially, when the parity information of this aspect of the invention is displayed on a monitor, the number of the partial data placed in the arranged direction may be reduced to the number corresponding to the width of the monitor, and the number of the partial data placed in the non-arranged direction may be increased. In this case, the sequence information can be displayed efficiently and plainly because the partial data placed in the non-arranged direction can be easily displayed on the monitor by scrolling it up and down on the screen of the monitor.

However, when the number of the partial data placed in the arranged direction is smaller than that of the partial data placed in the non-arranged direction, if the quantities of the first and second parity information are the same, the amount of data of the parity information increases as a whole. Thus, the amount of data of the parity information can be reduced and the differences between two sequences can be recovered efficiently by making the number of the parity information in the arranged direction (the second set of parity information) smaller than the number of the parity information in the non-arranged direction (the first set of parity information).

Moreover, the number of the partial data in the non-arranged direction is preferably smaller than or equal to $(2^m-1)/4$. As a result, since the partial data in the non-arranged direction can be multiplied by four different coefficients ($\alpha^k$, $\alpha^{2k}$, $\alpha^{3k}$, $\alpha^{4k}$), up to four differences (differences in the non-arranged direction) between two sequences for each column can be accurately recovered. This recovery seems to be enough for the detection and the like of ordinary SNP.

Moreover, in this aspect of the invention, the integer m, which defines Galois field $GF(2^m)$, is preferably a multiple of 64. Since the computers whose processing unit is 64 bits are increasing recently, the parity information can be efficiently computed by assuming that the integer m is a multiple of 64.

Then, the first method may further include the following steps: assuming that the sequence of the biological compounds is a standard sequence; computing two sets of parity information on a sequence of biological compounds under inspection correspondingly to the two sets of parity information on the standard sequence; and identifying the differences between the standard sequence and the sequence of biological compounds under inspection by using the four sets of parity information. Accordingly, the positions of the differences can be easily detected by comparing two sets of parity information on the standard sequence and two sets of parity information on the sequence under inspection. In addition, provided that the number of the differences for each column and each row is smaller than or equal to a predetermined number, the part of the standard sequence corresponding to the differences can be recovered correctly by solving the simultaneous equations based on four sets of parity information and the sequence of biological compounds under inspection.

According to another aspect of the invention, a device for recording sequence information on biological compounds, comprises the following components:

a sequencer (4) for reading sequence information on the biological compounds;

dividing means (10, step 105) for dividing the text data representing the sequence of the biological compounds or the numerical data obtained by converting the text data based on a conversion rule into plural m-bit partial data (A(i,j)) arranged in plural columns in the arranged direction corresponding to the direction along which the biological compounds are placed and in plural rows in the non-arranged direction which crosses the arranged direction, where m is an integer larger than or equal to 16;

computing means (10, step 106) for computing a first set of parity information by applying a first operation of Galois field $GF(2^m)$ along the non-arranged direction to a set of the partial data of each column and computing a second set of parity information by applying a second operation of Galois field $GF(2^m)$ along the arranged direction to a set of the partial data of each row; and recording means (15) for recording the first and second sets of parity information in a recording medium.

According to the device, the first method for recording sequence information on biological compounds such as nucleotides, amino acids, etc. can be carried out.

In the device for recording sequence information, when it is assumed that α is a primitive element of Galois field $GF(2^m)$, for example, the first set of parity information includes the sum of plural products obtained by multiplying a set of the partial data (A(i,j)) of each column along the non-arranged direction by $\alpha^{sp}, \alpha^{s(p+1)}, \alpha^{s(p+2)}, \ldots, \alpha^{s(p+dp)}$, where s and p are nonnegative integers and dp is an integer lager than or equal to one; and the second set of parity information includes the sum of plural products obtained by multiplying a set of the partial data of each row along the arranged direction by $\alpha^{tq}, \alpha^{t(q+1)}, \alpha^{t(q+2)}, \ldots, \alpha^{t(q+dq)}$, where t and q are nonnegative integers and dq is an integer lager than or equal to one.

Accordingly, the operations can be simplified because the coefficient by which the partial data (A(i,j)) is multiplied can be computed using only the primitive element α.

According to another aspect of the invention, a computer-readable medium (16) storing sequence information on biological compounds, comprises a data structure stored in the medium, wherein in order to form the data structure, the text data representing the sequence of the biological compounds or the numerical data obtained by converting the text data based on a conversion rule is divided into plural m-bit partial data arranged in plural columns in the arranged direction corresponding to the direction along which the biological compounds are placed and in plural rows in the non-arranged direction which crosses the arranged direction, where m is an integer larger than or equal to 16;

a first set of parity information is computed by applying a first operation of Galois field $GF(2^m)$ along the non-arranged direction to a set of the partial data of each column and a second set of parity information is computed by applying a second operation of Galois field $GF(2^m)$ along the arranged direction to a set of the partial data of each row; and the first and second sets of parity information are recorded in the data structure as the sequence information on the biological compounds.

According to the computer-readable medium, the parity information approximately representing the sequence information on biological compounds such as nucleotides and amino acids can be recorded in the medium in small amounts of data. Thus, such mediums as a CD-ROM, CD-R, flash-ROM, etc. whose memory capacity is relatively low but which are easy to use can also be used as the computer-readable medium.

In the computer-readable medium, the data structure preferably further includes a mathematical digest (message digest) of the text data representing the sequence of the biological compounds or the numerical data corresponding to the text data, where the size of the mathematical digest is larger than or equal to 40 bits.

The mathematical digest can be computed by applying a hash function such as the MD5 hash function (the size of the message digest is 128 bits) or the SHS (Secure Hash Standard) hash function (the size of the message digest is 160 bits) to the text data or the numerical data corresponding to the sequence of the biological compounds. It is easily confirmed with high accuracy whether two huge sequences of biological compounds are the same or not using the digest. Furthermore, after recovering the partial data differing from the counterparts by the use of the parity information, it can be confirmed whether the data has been recovered completely or not by comparing the mathematical digests. If the size of the mathematical digest is larger than or equal to 40 bits, for example, the sequence information of the nucleotides of the entire human race can be expressed almost without collisions.

In this aspect of the invention, when the integer m, which defines Galois field $GF(2^m)$, is a multiple of 64, the hash function whose message digest is of the size of a multiple of 64 bits, e.g. the MD5 hash function, is preferably used. In this case the calculation can be performed efficiently.

According to another aspect of the invention, a first method -for supplying sequence information on biological compounds comprises the following steps:

as the procedure of a supplier (2A), recording the text data representing the sequence of the biological compounds or the numerical data obtained by converting the text data based on a conversion rule in a first file (19) (step 104);

dividing the text data recorded in the first file or the numerical data recorded in the first file into plural m-bit partial data arranged in plural columns in the arranged direction corresponding to the direction along which the biological compounds are placed and in plural rows in the non-arranged direction which crosses the arranged direction, where m is an integer larger than or equal to 16;

computing a first set of parity information (B1(i) to B3(i)) by applying a first operation of Galois field $GF(2^m)$ along the non-arranged direction to a set of the partial data of each column and computing a second set of parity information (C1(j) to C3(j)) by applying a second operation of Galois field $GF(2^m)$ along the arranged direction to a set of the partial data of each row (steps 105,106);

recording the first and second sets of parity information in a second file (20) (step 107); and as the procedure of a user (2B), receiving the two sets of parity information recorded in the second file through a communications network (1) from the supplier (steps 110, 129).

According to the method for supplying sequence information, the above-mentioned method for recording sequence information on biological compounds is applied to a business model for supplying (selling) the sequence information thereon. That is, provided that the supplier has read the sequence of biological compounds such as nucleotides of the DNA or amino acids of the protein of a certain organism X first, the supplier computes the parity information approximately representing the sequence information in small amounts of data using the text data (or numerical data converted therefrom), then supplies the parity information to the user via the communications network. As noted above, since the size of the parity information is about 1/20 of that of the original text data, for example, the parity information can be received in a short time via the communications network.

The first method for supplying sequence information further preferably includes the following steps:

as the procedure of the user, identifying the differences between the sequence of the biological compounds held by the supplier and the sequence of biological compounds subject to examination based on the two sets of parity information (steps 130, 131); and when the differences cannot be recovered, the user receiving the sequence information on the part corresponding to the differences within the text data recorded in the first file or the numerical data recorded in the first file through the communications network from the supplier (step 135).

If the detection and recovery of the differences between the sequence under inspection and the sequence of the supplier can be performed using only the parity information, there is no need to purchase more information. On the other hand, when many differences exist and all of the corresponding sequences cannot be recovered correctly by using only the parity information, the user may purchase only the part of the text data which part cannot be recovered correctly. Consequently, necessary information is purchased through the communications network in a short time, and a relatively low-speed communications network like the cellular phone system can be used as the communications network.

In the method for supplying sequence information, when it is assumed that $\alpha$ is a primitive element of Galois field $GF(2^m)$, for example, the first set of parity information includes the sum of plural products obtained by multiplying a set of the partial data of each column along the non-arranged direction by $\alpha^{sp}, \alpha^{s(p+1)}, \alpha^{s(p+2)}, \ldots, \alpha^{s(p+dp)}$, where s and p are nonnegative integers and dp is an integer lager than or equal to one; and the second set of parity information includes the sum of plural products obtained by multiplying a set of the partial data of each row along the arranged direction by $\alpha^{tq}, \alpha^{t(q+1)}, \alpha^{t(q+2)}, \ldots, \alpha^{t(q+dq)}$, where t and q are nonnegative integers and dq is an integer lager than or equal to one.

The user can detect the SNP (Single Nucleotide Polymorphism) and the like easily using the parity information.

The method for supplying sequence information further preferably includes the following steps:

as the procedure of the supplier, letting the information on the number of the sequence of the biological compounds and the information on a mathematical digest of the text data or the numerical data be disclosed to the public through the communications network; and as the procedure of a user, accessing the information on the number of the sequence of biological compounds and the information on the mathematical digest through the communications network before receiving the two sets of parity information (step 121).

Accordingly, after computing the digest (message digest) of the text data (or numerical data converted therefrom) of the sequence of biological compounds of the organism X, the supplier discloses the digest on the Internet, for example. Thus, the supplier can assert that he is the first to read the sequence of the biological compounds of the organism X without disclosing the original text data, and the user can avoid purchasing the same sequence information from different suppliers.

Moreover, after purchasing the sequence information on the biological compounds from the supplier, a user computes the message digest of the purchased sequence information by applying the hash function and obtains the size of the sequence. Then, by comparing the size and the message digest with the corresponding values disclosed on the Internet, the user can check whether the purchased data is correct with high accuracy.

In the method for supplying sequence information, it is preferable that the size of the mathematical digest is 40 to 192 bits and the supplier further lets the information on a prescribed part of the sequence of the biological compounds be disclosed to the public through the communications network. By comparing the prescribed part, for example the top and end sequences of about 8 biological compounds with the corresponding sequences as well as the mathematical digest and the size of the sequence, the user can check whether the purchased data is the same as the original data with higher accuracy.

According to another aspect of the invention, a second method for recording sequence information on biological compounds comprises the following steps:

dividing the text data representing the sequence of the biological compounds or the numerical data obtained by converting the text data based on a conversion rule into plural m-bit partial data (A(i,j)) arranged in plural columns in the arranged direction corresponding to the direction along which the biological compounds are placed and in plural rows in the non-arranged direction which crosses the arranged direction, where m is an integer larger than or equal to 16;

assuming that a maximum value of the partial data is Nmax and a prime number larger than the maximum value Nmax is P;

computing a first set of parity information by applying a first operation of Galois field GF(P) along the non-arranged direction to a set of the partial data of each column;

computing a second set of parity information by applying a second operation of Galois field GF(P) along the arranged direction to a set of the partial data of each row; and representing the sequence information on the biological compounds by the first and second sets of parity information.

In this aspect of the invention, the biological compounds are supposed to be, for example, a series of nucleotides or a series of amino acids. The series of nucleotides are, for example, at least part of one chain of a pair of polymer chains constituting certain DNA, at least part of the polymer chain constituting certain RNA, or at least part of a gene. Then, in the case of FIG. 7, for example, the text data representing the sequence information on the biological compounds is divided into plural partial text data T(i,j) arranged in N columns (i=1 to N) in the arranged direction and in M rows (j=1 to M) in the non-arranged direction. Each of the partial text data T(i,j) is then converted into m-bit partial data A(i,j) as shown in FIG. 8. Each of the m-bit partial data A(i,j) represents the sequence of n (n=16 in the case of FIG. 8) consecutive biological compounds.

Next, plural pieces of data approximately representing the sequence information on each column and each row are computed by performing operations to each of the m-bit partial data A(i,j) in the non-arranged direction and the arranged direction, respectively. For the computation we need a field in which addition, subtraction, multiplication, and division of m-bit data can be performed. In a second method of the present invention Galois field GF(P) is used as the field. When Galois field GF(P) is used and the maximum value of the partial data A(i,j) is $(2^m-1)$, the prime number P needs to be an (m+1)-bit quantity. Thus, since a piece of information (which is referred to as "parity information" in the present invention) obtained by performing predetermined operations on Galois field GF(P) to the partial data of each column and each row respectively is expressed as an (m+1)-bit number, the size of each parity information increases by one bit. However, as a whole, the original sequence information is approximately represented by a set of parity information whose total size is almost as small as that obtained by using Galois field GF($2^m$). Moreover, according to this aspect of the invention, the operations used to compute the parity information are simpler than those on Galois field GF($2^m$).

In this aspect of the invention, the detection and recovery of the differences between two sequences can also be performed to some degree by comparing two sets of parity information of the two sequences.

In the second method for recording sequence information, the maximum value Nmax of the partial data is preferably smaller than ($2^{m-1}$). The easiest way of realizing this is to use the text data itself corresponding to the partial data A(i,j) as the partial data, which text data is considered as numerical data. In this case, the prime number P preferably satisfies the following condition:

$$2^m > P > Nmax. \qquad (A1)$$

This means that the prime number P is an m-bit number larger than the maximum value Nmax. Accordingly, since each of the parity information is expressed as m-bit data, the operations are simpler than those on Galois field GF($2^m$) and the size of all the parity information is the same as that obtained using Galois field GF($2^m$) at the same time.

In the second method for recording sequence information, when it is assumed that δ is a primitive element of Galois field GF(P), for example, the first set of parity information includes the sum of plural products obtained by multiplying a set of the partial data of each column along the non-arranged direction by $\delta^{sp}, \delta^{s(p+1)}, \delta^{s(p+2)}, \ldots, \delta^{s(p+dp)}$, where s and p are nonnegative integers and dp is an integer lager than or equal to one; and the second set of parity information includes the sum of plural products obtained by multiplying a set of the partial data of each row along the arranged direction by $\delta^{tq}, \delta^{t(q+1)}, \delta^{t(q+2)}, \ldots, \delta^{t(q+dq)}$, where t and q are nonnegative integers and dq is an integer lager than or equal to one. Accordingly, the parity information for each column and each row can be computed easily by adjusting the values of the integers s and t.

According to another aspect of the invention, a second method for supplying sequence information on biological compounds comprises the following steps:

as the procedure of a supplier (2A), recording the text data representing the sequence of the biological compounds or the numerical data obtained by converting the text data based on a conversion rule in a first file (19) (step 104);

dividing the text data recorded in the first file or the numerical data recorded in the first file into plural m-bit partial data arranged in plural columns in the arranged direction corresponding to the direction along which the biological compounds are placed and in plural rows in the non-arranged direction which crosses the arranged direction, where m is an integer larger than or equal to 16;

assuming that a maximum value of the partial data is Nmax and a prime number larger than the maximum value Nmax is P;

computing a first set of parity information by applying a first operation of Galois field GF(P) along the non-arranged direction to a set of the partial data of each column and computing a second set of parity information by applying a second operation of Galois field GF(P) along the arranged direction to a set of the partial data of each row;

recording the first and second sets of parity information in a second file (20); and as the procedure of a user (2B), receiving the two sets of parity information recorded in the second file through a communications network (1) from the supplier.

According to the second method for supplying sequence information, the above-mentioned second method for recording sequence information on biological compounds is applied to a business model for supplying (selling) the sequence information thereon. That is, provided that the supplier has read the sequence of biological compounds such as nucleotides of the DNA or amino acids of the protein of a certain organism X first, the supplier computes the parity information approximately representing the sequence information in small amounts of data using the text data (or numerical data converted therefrom), then supplies the parity information to the user via the communications network. In this method, since the amount of the parity information can be reduced to almost the same degree compared to the original text data as that computed using Galois field GF($2^m$), the parity information is received in a short time via the communications network.

The second method for supplying sequence information further preferably includes the following steps:

as the procedure of the user, identifying the differences between the sequence of the biological compounds held by the supplier and the sequence of biological compounds subject to examination based on the two sets of parity information; and when the differences cannot be recovered, the user receiving the sequence information on the part corresponding to the differences within the text data recorded in the first file or the numerical data recorded in the first file through the communications network from the supplier.

If the detection and recovery of the differences between the sequence under inspection and the sequence of the supplier can be performed using only the parity information, there is no need to purchase more information. On the other hand, when many differences exist and all of the corresponding sequences cannot be recovered correctly by using only the parity information, the user may purchase only the part of the text data which part cannot be recovered correctly. Consequently, necessary information is purchased through the communications network in a short time, and a relatively low-speed communications network like the cellular phone system can be used as the communications network.

BRIEF DESCRIPTION OF DRAWINGS

FIG. 7 is a diagram showing the text data of the nucleotide sequence (2048 nucleotides) of a standard sample E (DNA) where the text data is divided into plural partial text data T(i,j) in 4 columns and 32 rows;

FIG. 9 is a diagram showing the text data of the nucleotide sequence (2048 nucleotides) of a sample F (DNA) where the text data is divided into plural partial text data TF(i,j) in 4 columns and 32 rows;

FIG. 10 is a diagram of the partial data AF(i,j) of the sample F and the parities B1F(i) to C3F(j) computed therefrom;

FIG. 11 is a diagram of the parities of the sample F differing from the counterparts of the standard sample E and of the recovered partial data;

FIG. 12 is a flow chart showing the calculations for finding the values of the unknown data X1, X2, Y1, Y2 on Galois field $GF(2^{128})$;

FIG. 13 is a diagram showing the partial data B(i,j) arranged in 5 columns and 13 rows, which partial data are obtained by dividing the binary data converted from the text data of the nucleotide sequence of the standard sample E shown in FIG. 7;

FIG. 14 is a diagram showing the text data of the amino acid sequence (820 amino acids) of a sample G (protein) where the text data is divided into partial text data in 4 columns and 26 rows; and FIG. 15 is a diagram of the parities B1G(i) to C3G(j) computed from the amino acid sequence of FIG. 14.

BEST MODE FOR CARRYING OUT THE INVENTION

A preferred embodiment of the present invention will now be described with reference to the accompanying drawings. In this embodiment of the invention, some pieces of information on sequences of nucleotides (biological compounds) in DNA (deoxyribonucleic acid) are processed with computer systems.

Figure 1:
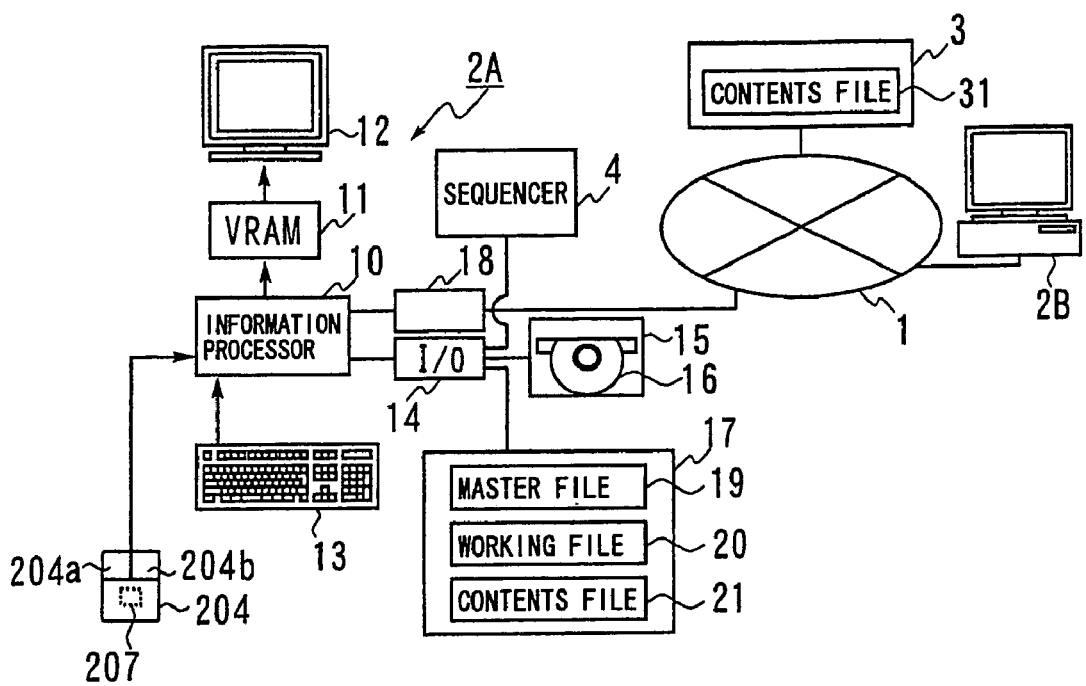
FIG. 1 is a schematic diagram of a computer system used in a preferred embodiment of the invention.

Referring to FIG. 1, which illustrates a computer system 2A of the embodiment, the computer system 2A has on its center an information processor 10 which consists of a CPU (central processing unit), memories such as RAM, ROM, etc., and storage devices including hard disk drives and the like. A display unit 12 consisting of a CRT display is connected to the information processor 10 via a video RAM (VRAM) 11, and a CD-R/RW drive 15 which can record data on a CD-Recordable disk (hereinafter referred to as "CD-R") 16 and read data in a CD-R and CD-ROM is connected to the information processor 10 via an I/O unit (input-output unit) 14. As a mass storage device a magnetic disk unit 17 with about several 100 GB memory is connected to the information processor 10 via the I/O unit 14.

The operating system and the application program to process sequence information on DNA as described below are installed in the hard disk drive of the information processor 10 of this embodiment through the CD-R/RW drive 15. Moreover, though the CD-R 16 corresponds to the readable medium of the present invention, a flash ROM, a flexible disk, a magneto-optical disk (MO), a digital video disc (DVD), a hard disk drive (for example, one built into the server which can be accessed through the Internet), etc. can be used as the readable medium as well as the CD-R and CD-ROM.

A keyboard 13 as the input device for character information, an optical mouse 204 as the pointing device (input device), and a communication control unit 18 consisting of a router (or a modem and so on) are also connected to the information processor 10. The mouse 204 comprises a displacement signal generator 207 that generates a signal indicating the position of a cursor on the screen of the display unit 12, a left switch 204a, and a right switch 204b. Those switches 204a, 204b (signal generators) generate signals designating information to be selected and various commands, etc. The computer system 2A comprises the information processor 10, the VRAM 11, the display unit 12, the keyboard 13, the mouse 204, the I/O unit 14, the CD-R/RW drive 15, the magnetic disk units 17, the communication control unit 18, etc. The Windows (registered trademark of Microsoft Corporation) is used as the operating system in this embodiment. The present invention can also be applied to the systems in which other operating systems such as UNIX (registered trademark of X/Open), OS/2 (registered trademark of IBM Corporation), MacOS (registered trademark of Apple Computer), and Linux (trademark or registered trademark of Linus Torvalds) are used.

Furthermore, the computer system 2A (the information processor 10) is connected to a communications network 1 consisting of the general telephone network via the communication control unit 18, and a provider 3 that presents various contents, a computer system 2B, a large number of servers (not shown), and other many computer systems (not shown) are connected to the communications network 1. The computer systems 2A, 2B and the provider 3 can communicate with one another through the Internet constructed on the communications network 1. In this embodiment, the owner of the computer system 2A is supposed to be a supplier (or a seller) of DNA information, and the owner of the computer system 2B is supposed to be a user (or a purchaser) of the DNA information. Thus, the application programs similar to those installed in the computer system 2A to process sequence information on DNA are installed to the latter computer system 2B in advance.

Now, a sequencer (DNA Sequencer) 4 that reads the sequence of a series of nucleotides (or the sequence of bases) in DNA as a sequence reader is connected to the information processor 10 in the computer system 2A of this embodiment through the I/O unit 14. The sequencer 4 reads the sequence of the nucleotides in one chain of a pair of polymer chains that constitute DNA using the Sanger method, for example. The Sanger method is disclosed in, for example, the reference 1 (Maxim D. Frank-Kamenetskii: Unraveling DNA (the most important molecule of life, revised and updated), translated by Lev Liapin, Chapter 6 (pp. 59-70) (Perseus Books, 1997)). The sequencer 4 memorizes the just-read sequence of the series of nucleotides in an internal mass storage device by the form of text data, and supplies the text data of a certain nucleotide sequence in the mass storage device to the information processor 10 through the I/O unit 14 at the request of the information processor 10. Accordingly, the information processor 10 processes the text data by means of the application programs to process sequence information on DNA as follows. Here it should be noted that a database of sequence information on nucleotides (or bases) constituting nucleic acids such as DNA and RNA (ribonucleic acid) can be used instead of the sequencer 4.

First of all, the first basic procedure of the information processor 10 of this embodiment will be described. The information processor 10 records the text data supplied by the sequencer 4 that represent the certain nucleotide sequence of DNA in a master file 19 defined in the magnetic disk unit 17 as it is. The information processor 10 then converts the text data into the numerical data having less data than the text data, and records the converted numerical data in a working file 20 defined in the magnetic disk unit 17.

In the following explanations, the number k in binary notation is described as bin(k) and the number in hexadecimal notation as hex(k).

In this case, DNA consists of four kinds of nucleotides, and the nucleotide including adenine, guanine, cytosine, or thymine as a base is represented respectively by the character A, G, C, or T in the text data supplied by the sequencer 4. Furthermore, the ASCII code of one byte (eight bits) consisting of hex(41), hex(47), hex(43), or hex(54) is allocated respectively to the character A, G, C, or T. As for RNA, the nucleotide including uracil is represented by the character U (hex(55)) instead of the nucleotide including thymine. Therefore, the text data representing the sequence of n nucleotides (n is an integer) will amount to the data of n bytes. The sequence of n nucleotides can be considered as the sequence of n bases (adenine, guanine, cytosine, and thymine (or uracil)).

In this embodiment, to express the text data by as less data as possible without reducing the amount of information, four kinds of nucleotides in DNA are represented by mutually different two-bit data. In DNA, one pair of bases (adenine and thymine) are mutually complementary and the other pair of bases (guanine and cytosine) are also mutually complementary. It is thus supposed that a pair of nucleotides whose bases are complementary are mutually complementary, and a pair of data each of which is the bit-wise complement of the other are allocated to one pair of complementary nucleotides including adenine and thymine respectively, and another pair of data each of which is the bit-wise complement of the other are allocated to the other pair of complementary nucleotides including guanine and cytosine respectively. Table 1 (the conversion table) is used to show the allocation of the data in this embodiment. Table 1 means that the character A, T (or U), G, or C in the text data representing the sequence of nucleotides is replaced respectively by bin(00), bin(11), bin(01), or bin(10).

TABLE 1

| Nucleotide | two-bit data |
|---|---|
| nucleotide including adenine (A) | bin(00) |
| nucleotide including thymine or uracil (T or U) | bin(11) |
| nucleotide including guanine (G) | bin(01) |
| nucleotide including cytosine (C) | bin(10) |

According to this embodiment, each nucleotide is represented by two-bit data, which is equivalent to representing each base by two-bit data. Moreover, the allocation of the data is not limited to Table 1. For example, the allocation may be used in which the nucleotide including thymine or adenine is represented respectively by bin(00) or bin(11), or the nucleotide including guanine or cytosine is represented respectively by bin(10) or bin(01). Besides, the data bin(01) and bin(10) may be allocated to the pair of nucleotides in which one includes adenine and the other includes thymine, and the data bin(00) and bin(11) may be allocated to the pair of nucleotides in which one includes guanine and the other includes cytosine. In the case of RNA, the same data that are given to the corresponding nucleotides in DNA are allocated to the nucleotides except that the data given to the nucleotide including thymine is allocated to the nucleotide including uracil.

Figure 2:
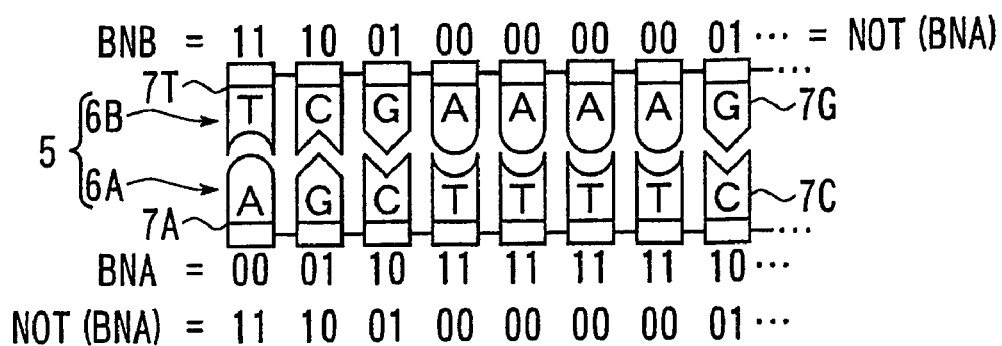
FIG. 2 is a diagram of a part of DNA processed in the preferred embodiment and an expression of the nucleotide sequence of the part of DNA in binary notation.
Figure 3:
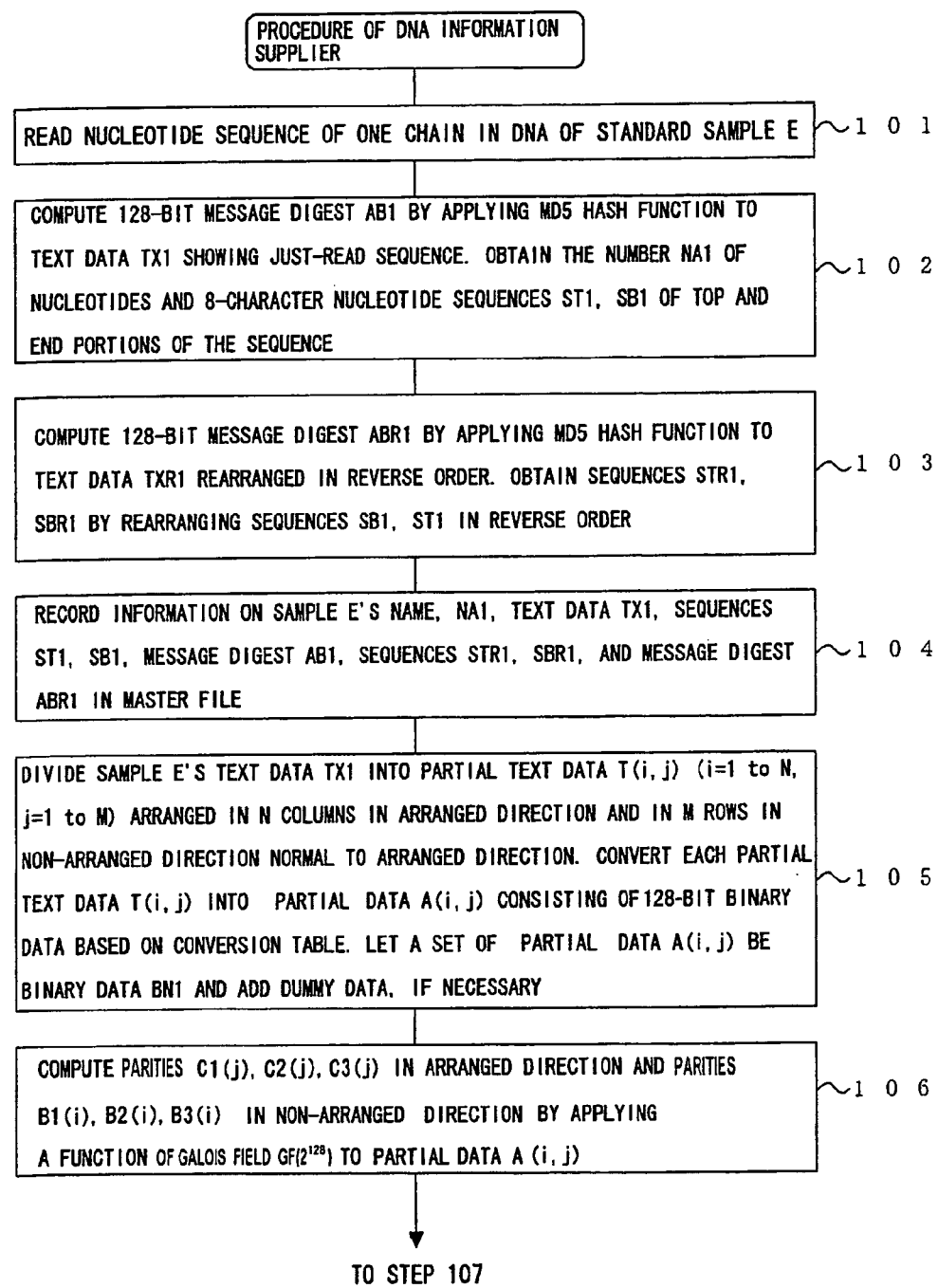
FIG. 3 is a flow chart showing part of the procedure of a DNA information supplier in the preferred embodiment.

Suppose that the sequence information on nucleotides of the DNA molecule 5 partly shown in FIG. 2 is processed in this embodiment. The sequence information is a part of the sequence information on a series of nucleotides of the DNA of *Escherichia coli* (*E. coli*), which was obtained from the website 1 (ftp://ncbi.nlm.nih.gov/genbank/genomes/bacteria/) offered by NCBI (The National Center for Biotechnology Information).

Referring to FIG. 2, the DNA molecule 5 consists of a pair of polymer chains 6A and 6B (a double helix), where one polymer chain 6A comprises four kinds of nucleotides, i.e. the nucleotide 7A with adenine, the nucleotide 7G with guanine, the nucleotide 7C with cytosine, and the nucleotide 7T with thymine, and the other polymer chain 6B is the nucleotide sequence complementary to the chain 6A. The text data representing the sequence of the polymer chain 6A are supplied to the information processor 10 of FIG. 1. The text data is supposed to be the data of a string of characters: "AGCTTT . . . ." Accordingly, after dividing the text data into blocks arranged in N columns and M rows (N and M are both integers of two or larger), the information processor 10 converts the characters A, G, C, and T in each block one by one into two-bit data using Table 1 (the conversion table). Thus, the information processor 10 obtains the binary data BNA (=bin(0001101111 . . . )) as numerical data. This binary data BNA is recorded in the working file 20 defined in the magnetic disk unit 17 of FIG. 1. The binary data BNA is reduced to ¼ of the original text data.

In this case, the data showing which nucleic acid (DNA or RNA) is recorded in the file, i.e. the data showing which character (T or U) the bin(11) should be interpreted as, the data showing the number of nucleotides, and other necessary data are preferably recorded in the top predetermined several bytes of the working file 20. Moreover, when the size of the working file 20 is a multiple of 1 byte (8 bits) and the binary data BNA have plural bytes and a fraction, the predetermined dummy data only have to be added to the end, which will hardly increase the amount of data. Then, for example, when the user (the owner of the computer system 2B) sends a purchase order for the sequence information on the DNA molecule 5 shown in FIG. 2 to the supplier (the owner of the computer system 2A), the data of the working file 20 is transmitted to the computer system 2B as an email attachment through the communications network 1 and a provider (not shown). In this case, the data of the working file 20 may be transmitted as a compression file (ZIP file, LHA file, etc.). The transmission time will be reduced to almost ¼ compared with the case when transmitting the original text data, since the data of the working file 20 is reduced to almost ¼ of the original text data. Thus, the communication costs of both the supplier and the user can be reduced.

Next, when the user wants to recover the text data showing the sequence of the polymer chain 6A in FIG. 2 from the received data of the working file 20, the computer system 2B will inversely convert the binary data BNA of the working file 20 into a string of the characters A, G, C, and T (or U) one by one by using Table 1. Moreover, for example, when the user needs also the text data showing the nucleotide sequence of the other complementary polymer chain 6B in FIG. 2, the computer system 2B will obtain the reversed binary data NOT(BNA) (=bin(1110010000 . . . )) as shown in FIG. 2 by getting the bit-wise complement of the binary data BNA. The reversed binary data NOT(BNA) is the same as the binary data BNB that is obtained by converting the text data (the string of characters "TCGAAA . . . ") which shows the nucleotide sequence of the other polymer chain 6B according to Table 1. Therefore, the computer system 2B can obtain the text data of the sequence of the complementary polymer chain 6B at an extremely high speed by inversely converting the reversed binary data NOT(BNA) into a string of the characters A, G, C, and T (or U) one by one according to Table 1. In this procedure, the bit-wise complement operation can be performed at an extremely high speed in usual computers. Furthermore, the operation for obtaining the bit-wise complement of any data can be replaced by, for example, the operation for computing the bit-wise exclusive-OR of the data and bin(111111 . . . ).

It should be noted that the supplier may record the content of the working file 20 in the CD-R 16 by means of the CD-R/RW drive 15 and send the CD-R 16 to the user by mail instead of transmitting the data of the working file 20 to the user through the communications network 1. For example, the sequence information on a complete set of human DNA (human genome) is expressed as about 3 GB text data. The text data can be converted into the binary data of ¾ GB, i.e. 750 MB as the numerical data of this embodiment by using Table 1. Since the capacity of the current CD-R and CD-ROM is about 650 MB, the binary data of about 750 MB can be recorded easily in the CD-R 16 by compressing a part or all of the binary data. On the other hand, when the data of about 750 MB is transmitted through the communications network 1, it might sometimes take too much transmission time today.

Moreover, each amino acid is determined by a sequence of three nucleotides, i.e. a codon. One or more 6-bit data representing each amino acid are thus obtained by expressing each nucleotide of the three nucleotides corresponding to the amino acid in 2-bit data. Then the data with the smallest value of all the 6-bit data corresponding to each amino acid may be chosen as the data representing the amino acid. Furthermore, since a piece of data whose size is a multiple of one byte is easy to handle, we may represent one amino acid by one-byte data that is obtained by adding two-bit discrimination data before or behind the 6-bit data. Accordingly, one advantage is that a set of common codes can be used in representing both nucleotides and amino acids.

Then, the second basic procedure of the information processor 10 of this embodiment will be described. In this embodiment, a mathematical digest (a message digest) is computed by applying a certain hash function to large text data (or the numerical data obtained by converting the text data according to Table 1) that represents a nucleotide sequence. In this embodiment, the MD5 hash function proposed by R. Rivest is used as the hash function. The MD5 hash function is disclosed in the website 2 (http://www.kleinscmidt.com/edi/md5.htm) offered by the network working group and Rivest. The algorithm of the MD5 hash function is also disclosed in WO 01/80431 A1. Moreover, the algorithms of the MD5 hash function and other hash functions disclosed in U.S. application Ser. No. 10/272,107, filed Oct. 16, 2002, are incorporated herein by reference. A 128-bit message digest is obtained by applying the MD5 hash function to text data (or a text file). In the future 64-bit CPUs will be used even in usual computers. Message digests of 128(=2·64) bits will thus be processed very easily. Furthermore massage digests of 192(=3·64) bits will also be processed easily.

In this embodiment, the program that was developed by RSA Data Security Inc. and is disclosed in the website 2 is used to apply the MD5 hash function.

As an example for using the message digests, the supplier of sequence information on DNA (or the information processor 10) reads the nucleotide sequence of DNA of a certain organism and computes the message digest of the text data representing the nucleotide sequence by applying the hash function. Then the supplier discloses the message digest on the Internet as well as the information showing the name of the organism and the location of the DNA. Consequently, the supplier seems to be able to declare that he was the first to decipher the DNA sequence of the organism without disclosing the whole text data. Afterwards, when a user sends a purchase order for the sequence information, the supplier converts the text data representing the nucleotide sequence into binary data by using Table 1, and transmits the binary data to the user, for example, by email through the communications network 1. Accordingly, the user inversely converts the binary data into the text data by using Table 1, and computes the message digest by applying the above-mentioned hash function to the inversely converted text data.

Furthermore, when both message digests computed by the user and disclosed by the supplier are equal, it is guaranteed with high accuracy that the purchased sequence information is equal to the sequence information held by the supplier. In addition, users can avoid buying the same pieces of sequence information from different suppliers by comparing the massage digests disclosed by the suppliers. In this case the accuracy with which two nucleotide sequences are equal can be improved by further comparing the size of both nucleotide sequences and short sequences, for example, top parts or end parts selected from both nucleotide sequences.

As a hash function the SHS (Secure Hash Standard) hash function proposed by NBS (National Bureau of Standards) and disclosed in the reference 2 (FIPS Publication 180,1993) can also be used. The SHS hash function has more complex operations than the MD5 hash function, and obtains the message digest of 160 bits. Since the number of amino acids constituting a protein, for example, is about 20-1000, and the text data corresponding to the amino acid sequence can be expressed in as small size as about 20 bytes to 1 KB using one-Letter code, the text data might be easily estimated from the message digest. Thus, when message digests of sequence information on amino acids are required, it is sometimes desirable to use the SHS hash function to prevent users from estimating the original text data.

Moreover, for example, when message digests need to be computed by applying a certain hash function in order just to confirm that the two large amounts of text data representing nucleotide sequences are equal, the hash function does not seem to be necessarily the one that performs a series of complex mathematical operations repeatedly. In such an application, for example, the MD4 hash function disclosed in the reference 3 (R. L. Rivest: "The MD4 message digest algorithm", Lecture Notes in Computer Science, 537,303-311(1991)) may be used. Moreover, in order just to confirm that the two sequences are equal, the size of the message digest may be sometimes as short as 40-128 bits.

Then, referring to the flow charts in FIGS. 3-6, a business model of this embodiment will be described in detail in which the supplier of DNA information (the computer system 2A) sends the sequence information on DNA to the user (the computer system 2B) in FIG. 1. First of all, in step 101 in FIG. 3, the supplier of DNA information makes the sequencer 4 read the nucleotide sequence of one chain of the DNA of a standard sample (hereinafter referred to as "the standard sample E"), and the text data TX1 representing the just-read nucleotide sequence are supplied to the information processor 10. In this embodiment, the standard sample E is supposed to be *E. coli*, whose sequence data was obtained from the website 1, and the text data showing the sequence of the first 2048 nucleotides of the DNA of *E. coli* is used as the text data TX1 as shown in FIG. 7.

The DNA sequence of the standard sample E is shown in SEQ ID NO:1 in Sequence Listing. The text data shown in FIG. 7 was generated by removing all numerical data from the sequence in SEQ ID NO:1 and replacing the characters a, g, c, and t respectively by the characters A, G, C, and T in the sequence.

Then, in step 102, the information processor 10 obtains a 128-bit message digest AB1 by applying the above-mentioned MD5 hash function to the supplied text data TX1. The information processor 10 then obtains the number NA1 of the nucleotides in the DNA sequence and two 8-character nucleotide sequences ST1 and SB1 taken respectively from the top and end portions of the text data TX1 as follows:

$$AB1=\text{hex}(849339ac244cde42b5346ab5989aab61),\quad(11)$$

NA1=2048,

ST1=AGCTTTTC, SB1=CGCGAAGG.

In the next step 103, the information processor 10 obtains the text data TXR1 (=GGAAGC ... TTTCGA) by rearranging the text data TX1 in reverse order, and then obtains the message digest ABR1 by applying the MD5 hash function to the text data TXR1. In addition, the information processor 10 obtains two 8-character nucleotide sequences STR1 and SBR1 corresponding respectively to the top and end portions of the text data TXR1 by rearranging the sequences SB1 and ST1 in reverse order. These values are as follows:

$$ABR1=\text{hex}(4eb1feae30f522642b912ce3ea09652b),\quad(12)$$

STR1=GGAAGCGC, SBR1=CTTTTCGA.

Then, in step 104, the information processor 10 records the information on the name of the standard sample E (the identifier of the sample), the number NA1, the text data TX1, the sequences ST1 and SB1, the message digest AB1, the reversed sequences STR1 and ABR1, and the message digest ABR1 of the reversed sequence in the master file 19 defined in the magnetic disk unit 17. In this case, the master file 19 may be divided into two or more files, and the text data TX1 and other data may be recorded in different files. Moreover, for example, when the size of the text data TX1 is more than or equal to about 100 MB, the text data TX1 may be divided into plural parts recorded in different master files.

In the subsequent step 105, the information processor 10 divides the text data TX1 of the standard sample E into plural partial text data T(i,j) (i=1 to N, j=1 to M) with 16 characters so that the partial text data T(i,j) are arranged in N columns in the arranged direction corresponding to the direction along which nucleotides are placed and in M rows in the direction (hereinafter referred to as "the non-arranged direction") normal to the arranged direction as shown in FIG. 7. Here, both of the numbers N and M are arbitrary integers larger than or equal to 2. As described above by referring to Equations 4 and 5, when the size of the text data TX1 is about 100 KB (or any multiple thereof) and the supplier needs the parity information whose size is reduced to about 1/20 of that of the text data TX1, the values of N and M are chosen such that N=64 and M=128, for example. In the following description, for simplicity, the text data TX1 is supposed to be divided in 4 columns and 32 rows, i.e. N=4 and M=32. In this case, no fraction is left. However, for example, if the number of characters of the last partial text data T(4,32) is smaller than 16 in FIG. 7, one or more predetermined characters (for example, the character "A") have only to be added to the empty part of the last partial text data as dummy data. Moreover, the size of the partial text data T(i,j) may be other than 16 characters. However, in order to improve the processing speed, the size of the partial text data T(i,j) is preferably any multiple of 8 characters.

In addition, the information processor 10 converts each of the partial text data T(i,j) with 16 characters in FIG. 7 into partial data A(i,j) which consists of 128(=16×8)-bit binary data (the numerical data) respectively based on a predetermined conversion table. In this embodiment, a function asc(T(i,j)) is used as the conversion table, which function simply converts the partial text data T(i,j) into the ASCII codes as follows:

$$A(i,j)=\text{asc}(T(i,j))\quad(13)$$

Figure 8:
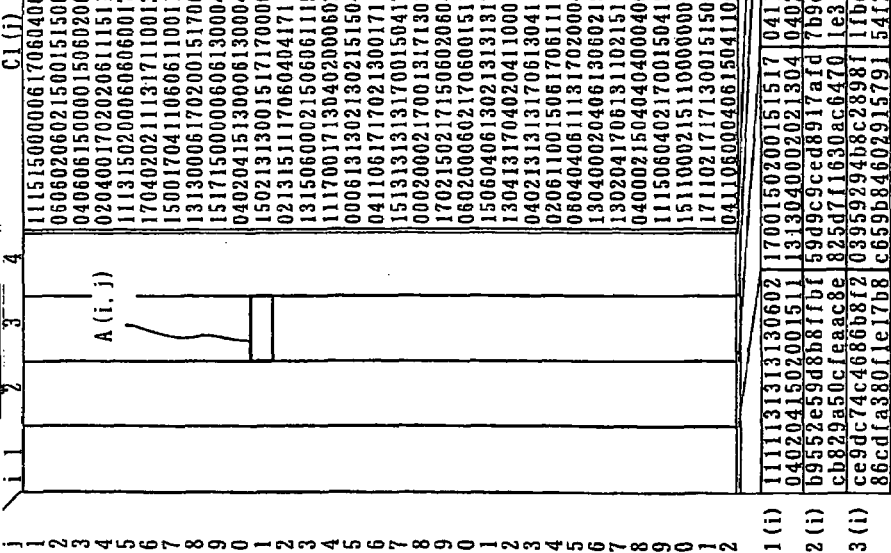
FIG. 8 is a diagram of the partial data A(i,j) of the standard sample E and the parities B1(i) to C3(j) computed therefrom.

It should be noted that the function asc(T(i,j)) converts the partial text data T(i,j) so that the codes of the characters at the front and end of the partial text data are placed in the least and most significant parts, respectively, as shown by the converted example of T(3,11) in FIG. 7. In this case, if the partial data A(i,32) in the last row includes less than 128-bit code data, the dummy data such as predetermined character codes or numerical data representing 0 (hex(000 ... )) is added to the most significant part of partial data. Consequently, all of the partial data A(i,j) are arranged in 4 columns and 32 rows as shown in FIG. 8. Moreover, a set of data (the numerical data) obtained by arranging all of the partial data A(i,j) consecutively in the direction corresponding to the direction along which nucleotides are placed is referred to as the binary data BN1. The partial text data T(i,j) in FIG. 7 has substantially the same amount of data as the partial data A(i,j) in FIG. 8.

Then, in this embodiment, a certain operation on Galois field $GF(2^m)$ is applied to the partial data A(i,j) by considering the partial data A(i,j) to be an element of Galois field $GF(2^m)$ in vector representation. Since the size of the partial data A(i,j) of this embodiment is 128 bits, the value of m is 128 (twice as large as 64) and Galois field $GF(2^{128})$ is used. Moreover, in this embodiment, the following polynomials are used as an irreducible polynomial GF(X) and a primitive element α on Galois field $GF(2^{128})$. Galois field $GF(2^m)$ may be called an extension Galois field.

$$GF(X)=1+X^{121}+X^{126}+X^{127}+X^{128}\quad(14)$$

$$\alpha=X\quad(15)$$

GF(X) and α are expressed as bin(1110000100...01) and bin(00 ... 0010), respectively, in vector representation of Galois field $GF(2^{128})$. A polynomial (1+X) and the like can be used as the primitive element α. Moreover, the following irreducible polynomial GF'(X) can also be used, for example, as another irreducible polynomial on Galois field $GF(2^{128})$, and the following element α' can be used as a primitive element corresponding to the irreducible polynomial GF'(X).

$$GF'(X)=1+X^{11}+X^{124}+X^{125}+X^{126}+X^{127}+X^{128}\quad(14A)$$

$$\alpha'=1+X+X^2\quad(15A)$$

Moreover, the easiest method of confirming the irreducibility of the polynomial GF(X) is to divide the polynomial GF(X) by all possible polynomials whose degree is less than or equal to m', where m' is the integer not exceeding m/2. In this method, if there is no polynomial dividing the polynomial without a remainder, the polynomial GF(X) is irreducible.

Furthermore, provide that the degree m is large, the irreducibility of the polynomial GF(X) can be confirmed, for example, by "the method of Kronecker" disclosed in reference 4 (Van der Waerden, B. L. (1953), Modern Algebra (2 vols.), p. 77, Ungar, N.Y.). A practical method of confirming the irreducibility of the polynomial GF(X) is to use the built-in function "POLFACT2" in the "UBASIC", which is a software for studying the number theory and which is disclosed in website 3 (http://archives.math.utk.edu/software/msdos/number.theory/ubasic/.html) or in website 4 (http://www.rkmath.rikkyo.ac.jp/~kida/ubasic.htm).

Then, assuming that $k=2^m-1$, the primitive element $\alpha$ of Galois field $GF(2^m)$ satisfies the following relations modulo the irreducible polynomial GF(X):

$$\alpha^k = 1 (\mod GF(X)), \tag{16}$$

$$\alpha^{k'} \neq 1 (\mod GF(X)) (1 \leq k' < k). \tag{17}$$

Suppose that the integer k can be factorized as follows using prime numbers p1, p2, ..., pr and integers n1, n2, ..., nr:

$$k = 2^m - 1 = p1^{n1} \cdot p2^{n2} \ldots pr^{nr}. \tag{18}$$

Then, the primitive element $\alpha$ is determined so that all of $\alpha$ to the power of $(p1^{n1-1} \cdot p2^{n2} \ldots pr^{nr})$, $\alpha$ to the power of $(p1^{n1} \cdot p2^{n2-1} \ldots pr^{nr})$, ..., and $\alpha$ to the power of $(p1^{n1} \cdot p2^{n2} \ldots pr^{nr-1})$ do not come to 1 modulo the irreducible polynomial GF(X).

Moreover, since an arbitrary nonzero element $\beta$ of Galois field $GF(2^m)$ satisfies equation (16), the inverse element $\beta^{-1}$ of $\beta$ can be computed as follows by the use of $k(=2^m-1)$:

$$\beta^{-1} = \beta^{k-1} (\mod GF(X)). \tag{16R}$$

Therefore, for example, when the partial data A(i,j) is divided by $\beta$, we have only to multiply the partial data A(i,j) by $\beta^{k-1}$.

In the next step 106, the information processor 10 computes the first parity B1(i), the second parity B2(i), and the third parity B3(i) for the partial data A(i,j) of each column (i=1 to 4) shown in FIG. 8 by adding up all the partial data A(i,j), calculating the sum $\Sigma \alpha^{(j-1)} A(i,j)$, and calculating the sum $\Sigma \alpha^{2(j-1)} A(i,j)$, respectively, along the non-arranged direction (j=1 to 32) of each column on Galois field $GF(2^{128})$. These parities B1(i) to B3(i) in the non-arranged direction (the first set of parity information) are expressed as follows using the primitive element $\alpha$ and by performing the operations modulo the irreducible polynomial GF(X). The $\Sigma$ in parities B1(i) to B3(i) denote the summation over the range 1 to 32 of j, and the following equations are computed for the range 1 to 4 of i:

$$B1(i) = \Sigma A(i,j) = A(i,1) + A(i,2) + \ldots + A(i,32), \tag{19}$$

$$B2(i) = \Sigma \alpha^{(j-1)} \cdot A(i,j) = A(i,1) + \alpha \cdot A(i,2) + \ldots + \alpha^{31} \cdot A(i,32), \tag{20}$$

$$B3(i) = \Sigma \alpha^{2(j-1)} \cdot A(i,j) = A(i,1) + \alpha^2 \cdot A(i,2) + \ldots + \alpha^{62} \cdot A(i,32). \tag{21}$$

In this case, the parity B1(i) in equation (19) expressed in vector expression is the same as the result obtained by performing a bit-wise exclusive-OR operation to the partial data A(i,j). The parities B2(i) and B3(i) in equations (20) and (21) are computed by representing each partial data A(i,j) by a polynomial like equation (1) whose degree is less than or equal to 127 (m=128) and performing the operations modulo the irreducible polynomial GF(X).

In addition, the information processor 10 computes the first parity C1(j), the second parity C2(j), and the third parity C3(j) for the partial data A(i,j) of each row (=1 to 32) shown in FIG. 8 by adding up all the partial data A(i,j), calculating the sum $\Sigma \alpha^{(i-1)} \cdot A(i,j)$, and calculating the sum $\Sigma \alpha^{2(i-1)} \cdot A(i,j)$, respectively, along the arranged direction (i=1 to 4) of each row on Galois field $GF(2^{128})$. These parities C1(j) to C3(j) in the arranged direction (the second set of parity information) are expressed as follows using the primitive element $\alpha$ and by performing the operations modulo the irreducible polynomial GF(X). The $\Sigma$ in parities C1(j) to C3(j) denote the summation over the range 1 to 4 of i, and the following equations are computed for the range 1 to 32 of j:

$$C1(j) = \Sigma A(i,j) = A(1,j) + A(2,j) + \ldots + A(4,j), \tag{22}$$

$$C2(j) = \Sigma \alpha^{(i-1)} \cdot A(i,j) = A(1,j) + \alpha \cdot A(2,j) + \ldots + \alpha^3 \cdot A(4,j), \tag{23}$$

$$C3(j) = \Sigma \alpha^{2(i-1)} \cdot A(i,j) = A(1,j) + \alpha^2 \cdot A(2,j) + \ldots + \alpha^6 \cdot A(4,j). \tag{24}$$

The parities B1(i) to B3(i) and C1(j) to C3(j) actually computed by using the partial data A(i,j) are shown in vector representation of hexadecimal notation in FIG. 8. In this embodiment, since the number of the parities B1(i) to B3(i) of each column and the number of the parities C1(j) to C3(j) of each row are three, respectively, up to three partial data A(i,j) differing from the counterparts can be recovered correctly for each column and each row by comparing two nucleotide sequences. Thus, if the detection (identification) of the partial data A(i,j) differing from the counterparts can be performed and only one different partial data has to be recovered, the parities B1(i) and C1(j) or the parities B2(i) and C2(j) may be used as the parity information. One advantage of using only the latter parities B2(i) and C2(j) is that if two partial data A(i,j) are exchanged in a column or row, for example, the position of the difference between two sequences can be detected.

If up to two different partial data A(i,j) have only to be recovered for each column and each row, any two selected from parities B1(i), B2(i), B3(i) and any two selected from parities C1(j), C2(j), C3(j) may be used (computed) as the first and second sets of parity information, respectively. Furthermore, if the numbers of the different partial data to be recovered of each column and of each row may be different from each other, the numbers of the parities of the first and second sets of parity information may be different from each other. In addition, more than or equal to four different partial data have to be recovered correctly for each column and each row, for example, the parity Bs(i) (s=4, 5, ...) expressed as $\Sigma \alpha^{s(j-1)} \cdot A(i,j)$ and the parity Ct(j) (t=4, 5, ...) expressed as $\Sigma \alpha^{t(i-1)} \cdot A(i,j)$ have only to be computed, respectively.

Suppose that the partial data A(i,j) in FIG. 8 are arranged in 64 columns and 128 rows, then in order to recover up to three different partial data for each column and each row using parities B1(i) to B3(i) and C1(j) to C3(j), each of which is a 128-bit (16-byte) quantity, as shown in FIG. 8, the amount of data of all parity information needs to be 576·16 (=(64+128)·3·16) bytes. On the other hand, the amount of data of all partial data A(i,j) is 8192·16(=64·128·16) bytes. The total data of all parity information is thus reduced to almost 1/14 of that of all the partial data A(i,j).

Figure 4:
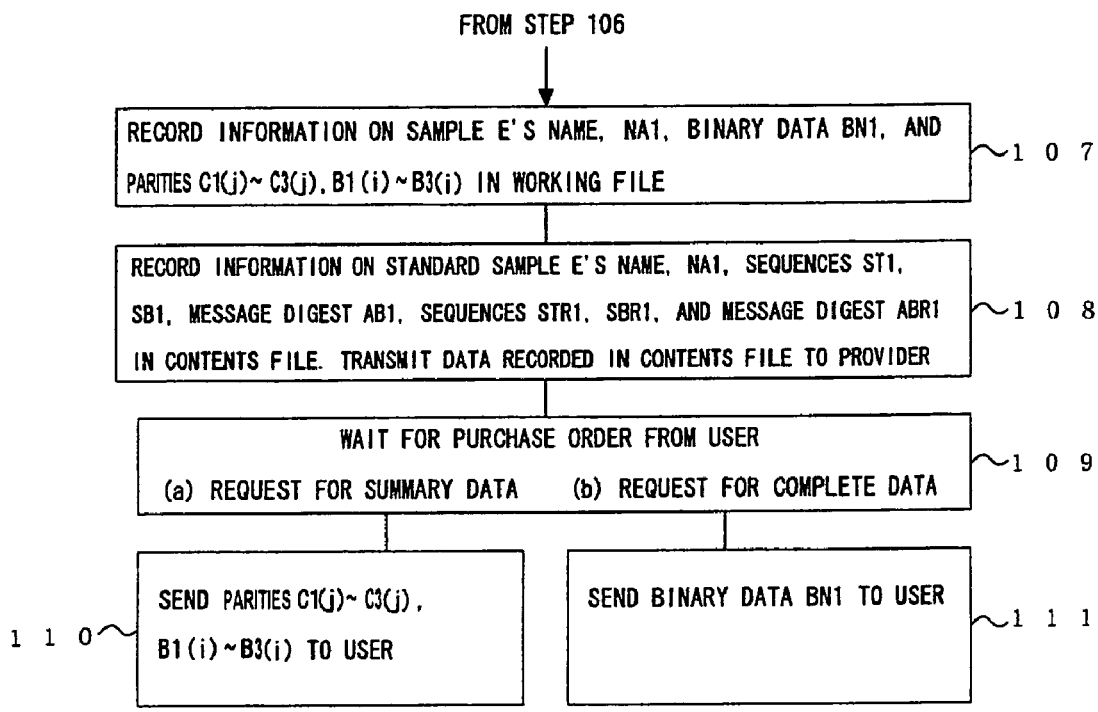
FIG. 4 is a flow chart of the procedure of the supplier following the steps of FIG. 3.

In the subsequent step 107 in FIG. 4, the information processor 10 records the information on the name of the standard sample E, the number NA1, the binary data BN1, and the parities B1(i) to B3(i), C1(j) to C3(j) in the working file 20 defined in the magnetic disk unit 17. In this case, the working file 20 may be divided into two or more files, and the binary data BN1 and the parities B1(i) to B3(i), C1(j) to C3(j) may be recorded in different files. The message digest AB1 computed in step 102 may be recorded in the working file 20 as well as the binary data BN1.

When the size of the binary data BN1 is large, the binary data BN1 may be divided into two or more parts, which may be recorded in plural files. In addition, when the size of the text data TX1 in FIG. 7 (therefore, the binary data BN1 in FIG. 8) is considerably large, the text data TX1 may be divided into two or more data groups of about 100 KB, and the parities B1(i) to B3(i), C1(j) to C3(j) may be computed for each data group.

Furthermore, also in step 107, the information recorded in the working file 20, i.e. the information on the name of the standard sample E, the number NA1, the binary data BN1, and the parities B1(i) to B3(i), C1(j) to C3(j), and the information on the massage digest AB1, ABR1 recorded in the master file 19 may be recorded in the CD-R 16 by means of the CD-R/RW drive 15 under the control of the supplier of DNA information. In addition, the supplier may reproduce the CD-R 16 on many CD-ROMs, and sell these recording mediums to users by mail and the like.

Then, in step 108, the information processor 10 records the information on the name of the standard sample E, the number NA1, the sequences ST1 and SB1, the message digest AB1, the reversed sequences STR1 and SBR1, and the message digest ABR1 of the reversed sequence in a contents file 21 defined in the magnetic disk unit 17. Even if the size of the text data TX1 in FIG. 7 is as large as about 100 MB, the size of the data recorded in the contents file 21 is as small as about 500 bytes. The information processor 10 then transmits the information recorded in the contents file 21 to the contents provider 3 through the communications network 1. Consequently, the information in the contents file 21 is recorded in the contents file 31, which is defined in the server of the provider 3 and is freely accessible, and the information in the contents file 21 has become disclosed to the public via the Internet.

In the next step 109, the supplier of DNA information enters the state to wait for purchase orders from users. When, as a case (a), a user sends a purchase order for the summary data of the standard sample E, the procedure moves to step 110, and the information processor 10 transmits the parity information (parities B1(i) to B3(i), C1(j) to C3(j)) in the working file 20 defined in the magnetic disk unit 17 to the user as an email attachment, for example. On the other hand, when, as a case (b) in step 109, a user sends a purchase order for the complete data, the procedure moves to step 111. Here the information processor 10 compresses the binary data BN1 in the working file 20 into the data such as a ZIP file and the like, and transmits the compressed data to the user as an email attachment, for example. In this case (b), the information processor 10 may transmit the message digest AB1 computed by the hash function as well, if necessary. According to this embodiment, since the size of the summary data (the parity information) is small, the summary data can be transmitted in a short time.

Also in step 109, the user may purchase only part of all data, i.e. necessary data (for example, only the two partial data A(4,16) and A(1,17)) selected from all the partial data A(i,j) in FIG. 8 from the supplier, if necessary. Hence only necessary and accurate data can be purchased in a short time.

Figure 5:
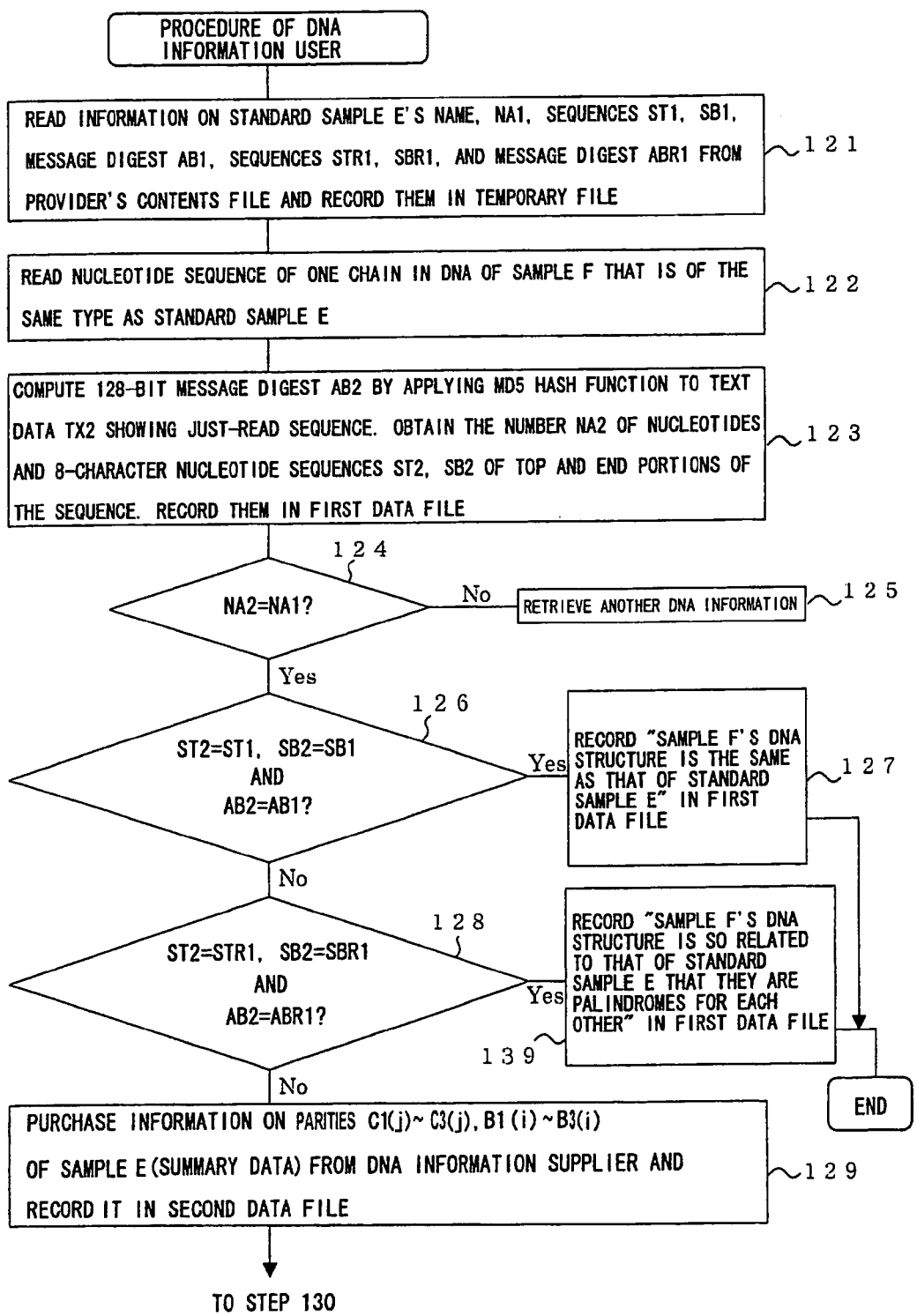
FIG. 5 is a flow chart showing part of the procedure a user of DNA information in the preferred embodiment.

Then, in step 121 in FIG. 5, the user of DNA information (the owner of the computer system 2B in FIG. 1) accesses the contents file 31 in the server of the provider 3 through the communications network 1 (the internet) in FIG. 1. The user then reads the information transmitted by the supplier in step 108, i.e. the information on the name of the standard sample E, the number NA1 of nucleotides, the sequences ST1 and SB1, the message digest AB1, the reversed sequences STR1 and SBR1, and the message digest ABR1 of the reversed sequence from the contents file 31, and the user records the just-read information in the temporary file defined in a memory device of the computer system 2B.

In the subsequent step 122, the user reads the sequence of nucleotides of one chain of the DNA of the sample F under inspection by means of a DNA sequencer (not shown), where the sample F is of the same type as the standard sample E. The user then transfers the text data TX2 (which is assumed to be expressed in ASCII codes) representing the just-decoded sequence to the information processor of the computer system 2B. The sample F under inspection is, for example, an *E. coli* that seems to have mutated, and the text data TX2 is supposed to represent the sequence of the first 2048 nucleotides in the same way as the text data TX1 of the standard sample E.

The DNA sequence of the sample F is shown in SEQ ID NO:2 in Sequence Listing. The text data shown in FIG. 9 described below was generated by removing all numerical data from the sequence in SEQ ID NO:2 and replacing the characters a, g, c, and t respectively by the characters A, G, C, and T in the sequence.

Figure 9:
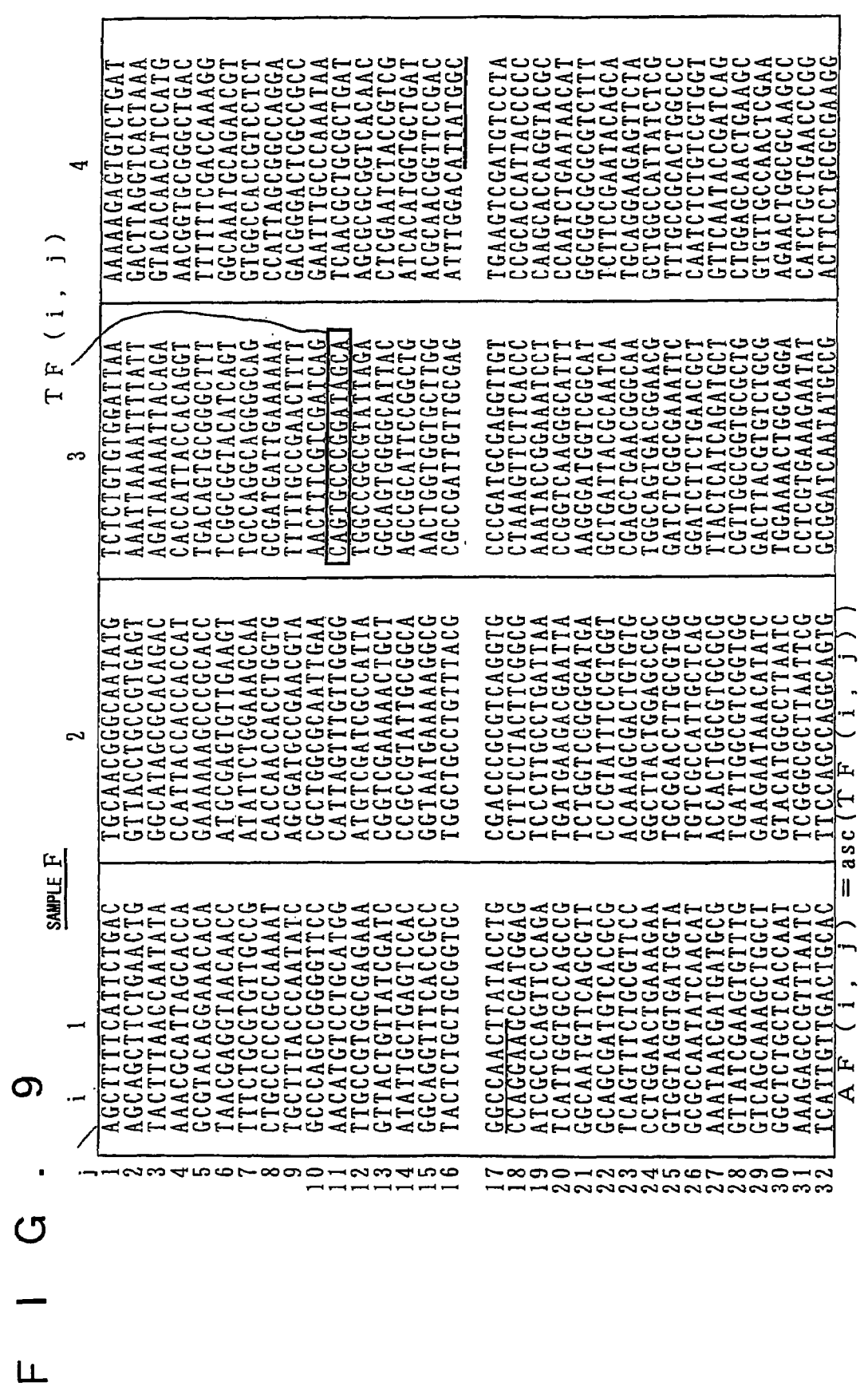

FIG. 9 shows the text data TX2 corresponding to the nucleotide sequence of the DNA of the sample F; and only the underlined portions of the sequence shown in FIG. 9 are different from the sequence of the standard sample E shown in FIG. 7. That is, of the sequence of the sample F only the portions corresponding to the partial text data T(4,16) and T(1,17) of the standard sample E are different as follows. At this stage, it is not known to the user which part of the sequence of the sample F is different from that of the standard sample E.

| the standard sample E | | the sample F |
|---|---|---|
| T(4, 16) = ATTTGGACGGACGTTG | → | ATTTGGAC<u>ATTATGGC</u> |
| T(1, 17) = ACGGGGTCTATACCTG | → | <u>GGCCAACT</u>TATACCTG |

Now, the application program to process sequence information on DNA is started in the information processor of the user's computer system 2B. Then, in step 123, the information processor computes the 128-bit message digest AB2 by applying the above-mentioned MD5 hash function to the just decoded text data TX2. The information processor also obtains the number NA2 of nucleotides of the sequence and two 8-character nucleotide sequences ST2 and SB2 corresponding respectively to the top and end portions of the sequence, and records these data in the first data file defined in a built-in storage device. These values corresponding to the text data TX2 (FIG. 9) are as follows:

$$AB2 = \text{hex}(1457b51222a83c3222e87cb4d4e63305), \quad (25)$$

$$NA2 = 2048,$$

$$ST2 = \text{AGCTTTTC}, \quad SB2 = \text{CGCGAAGG}.$$

In the next step 124, the information processor checks whether the number NA2 of the sample F and the number NA1 of the standard sample E are equal, and if they are different, the procedure of the user moves to step 125, and the user retrieves another DNA information to find out the DNA information on the sequences each having nucleotides that amount to the same number as NA2. In this embodiment, since NA2=NA1 in step 124, the procedure moves to step 126, and the information processor checks whether the sequences ST2 and SB2 of the top and end portions of the sample F are equal to the sequences ST1 and SB1 of the standard sample E respectively. The information processor also checks whether the message digest AB2 of the sample F is equal to the message digest AB1 of the standard sample E (which is recorded in the temporary file in step 121). If both checks are affirmative, it is affirmative in extremely high probability (the error rate is nearly $\frac{1}{2}^{128} \approx \frac{1}{10}^{38}$) that the sequence of the sample F matches the sequence of the standard sample E. In this case, the procedure moves to step 127, and the information processor of the computer system 2B records the information indicating that "the DNA structure of the sample F is the same as that of the standard sample E" in the first data file.

However, in this embodiment, although it is satisfied that ST2=ST1 and SB2=SB1, it is clear that AB2≠AB1 from equations (11) and (25). The procedure thus moves from step 126 to step 128, and the information processor checks whether the sequences ST2 and SB2 of the top and end portions of the sample F are equal to the sequences STR1 and SBR1 of the reversed sequence of the standard sample E respectively. The information processor also checks whether the message digest AB2 of the sample F is equal to the message digest ABR1 of the reversed sequence of the standard sample E. If both checks are affirmative, it is considered in extremely high probability that the sequence of the sample F matches the reversed sequence of the standard sample E. In this case, the procedure moves to step 139, and the information processor of the computer system 2B records the information indicating that "the DNA structure of the sample F is related to that of the standard sample E in such a way that they are palindromes to each other" in the first data file.

In this embodiment, since ST2≠STR2, SB2≠SBR2, and it is clear that AB2≠ABR1 from equations (12) and (25), the procedure moves from step 128 to step 129. Here the user purchases the above-mentioned summary data, i.e. the parity information (B1(i) to B3(i), C1(j) to C3(j)) of the standard sample E (the information shown in FIG. 8) from the supplier of DNA information through the communications network 1 (the internet), and the user records the purchased information in the second data file defined in the memory unit of the computer system 2B (the information processor).

Figure 6:
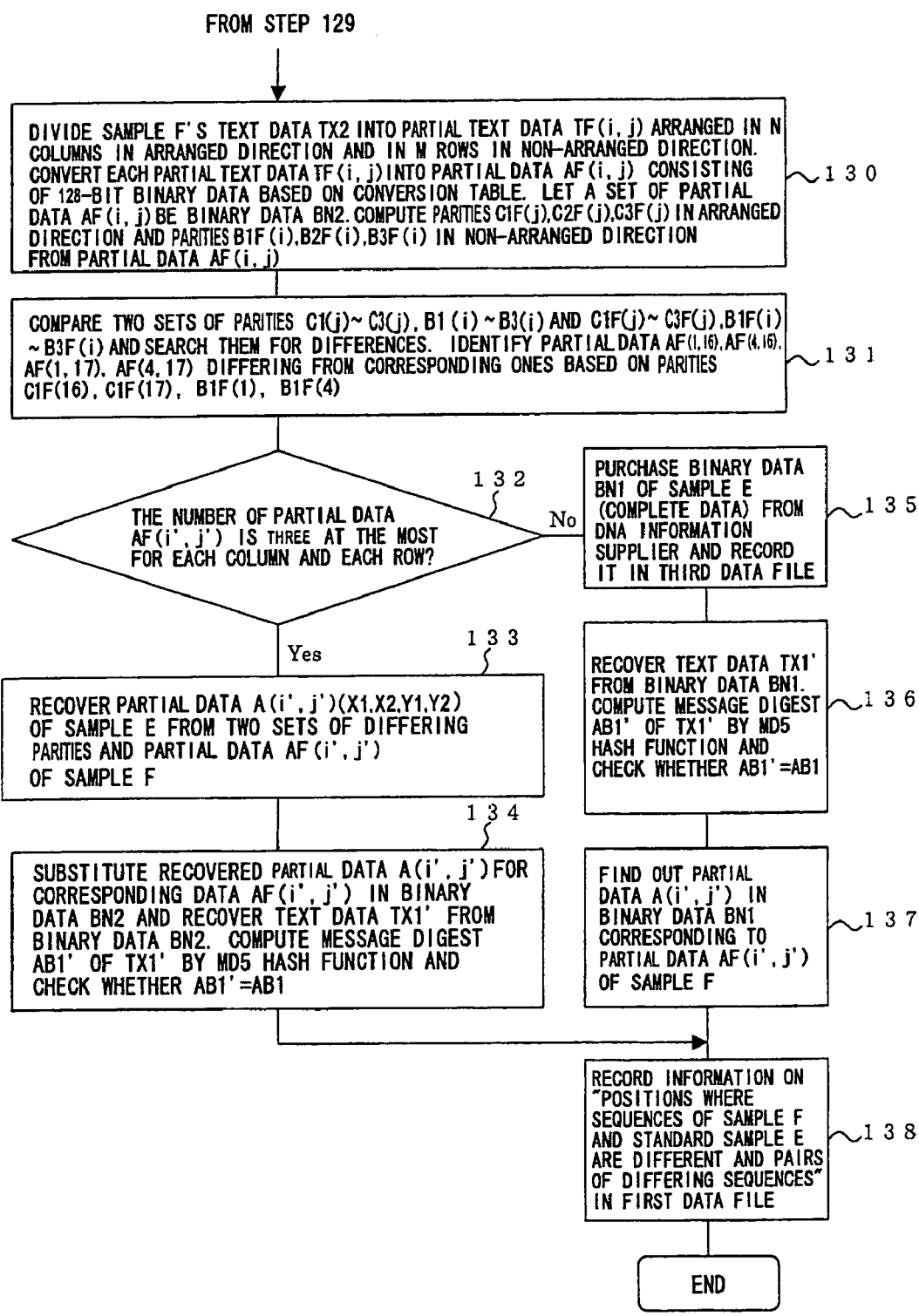
FIG. 6 is a flow chart of the procedure of the user following the steps of FIG. 5.

Then, in step 130 in FIG. 6, the information processor of the computer system 2B divides the text data TX2 of the sample F into plural 16-character partial text data TF(i,j) (i=1 to N, j=1 to M) arranged in N columns in the arranged direction (corresponding to the direction along which nucleotides are placed) and in M rows in the non-arranged direction as shown in FIG. 9. The numbers N and M of division are the same as those of the standard sample E, and it is supposed that N=4, M=32 in this embodiment. In addition, the information processor converts each partial text data TF(i,j) in FIG. 9 into the partial data AF(i,j) consisting of 128(=16·8)-bit binary data (numerical data) using the following function asc(TF(i,j)), which simply converts the text data into the ASCII codes. In this case, the characters corresponding to the partial text data TF(i,j) are also converted to a string of ASCII codes in reversed order.

$$AF(i,j)=asc(TF(i,j)) \quad (26)$$

Figure 10:
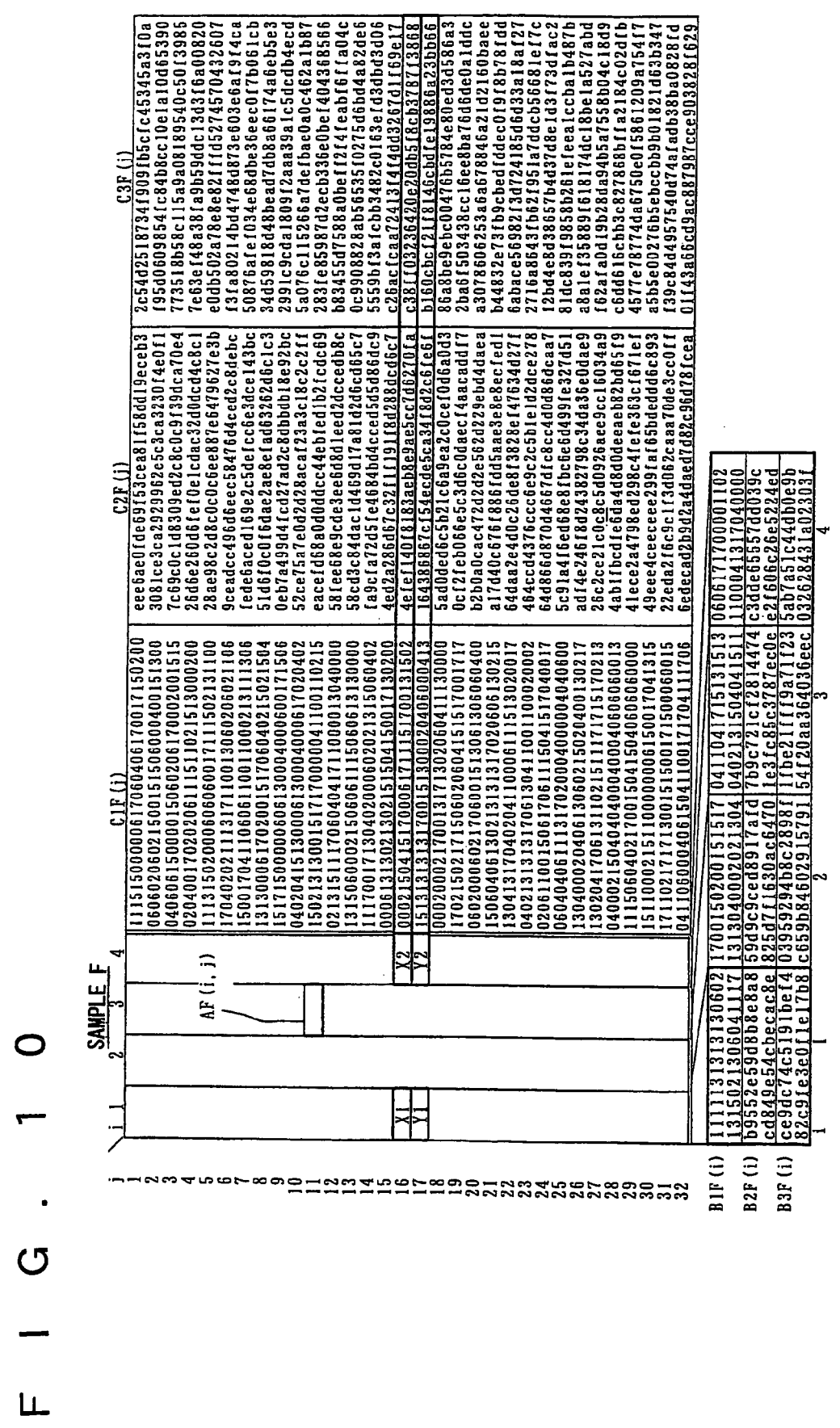

The partial data AF(i,j) arranged in 4 columns and 32 rows are thus obtained as shown in FIG. 10. A set of data (the numerical data) obtained by arranging all of the partial data AF(i,j) consecutively are referred to as the binary data BN2.

In the same way as the procedure of step 106, the information processor then computes the first parity B1F(i), the second parity B2F(i), and the third parity B3F(i) for the partial data AF(i,j) of each column (i=1 to 4) shown in FIG. 10 by adding up all the partial data AF(i,j), calculating the sum $\Sigma\alpha^{(j-1)}\cdot AF(i,j)$, and calculating the sum $\Sigma\alpha^{2(j-1)}\cdot AF(i,j)$, respectively, along the non-arranged direction (j=1 to 32) of each column on Galois field $GF(2^{128})$. These parities B1F(i) to B3F(i) in the non-arranged direction (the first set of parity information) are computed using the primitive element α of equation (15) and by performing the operations similar to equations (19) to (21) modulo the irreducible polynomial GF(X) for the range 1 to 4 of i.

The information processor then computes the first parity C1F(j), the second parity C2F(j), and the third parity C3F(j) for the partial data AF(i,j) of each row (j=1 to 32) shown in FIG. 10 by adding up all the partial data AF(i,j), calculating the sum $\Sigma\alpha^{(i-1)}\cdot AF(i,j)$, and calculating the sum $\Sigma\alpha^{2(i-1)}\cdot AF(i,j)$, respectively, along the arranged direction (i=1 to 4) of each row on Galois field $GF(2^{128})$. These parities C1F(j) to C3F(j) in the arranged direction (the second set of parity information) are computed using the primitive element α of equation (15) and by performing the operations similar to equations (22) to (24) modulo the irreducible polynomial GF(X) for the range 1 to 32 of j.

The parities B1F(i) to B3F(i) and C1F(j) to C3F(j) actually computed by using the partial data AF(i,j) are shown in vector representation of hexadecimal notation in FIG. 10.

In the next step 131, the information processor compares the two sets of parities in the summary data purchased from the supplier, i.e. two sets of parities B1(i) to B3(i) and C1(j) to C3(j) in FIG. 8 (of the standard sample E) with two sets of parities B1F(i) to B3F(i) and C1F(j) to C3F(j) in FIG. 10 (of the sample F), and the information processor searches them for the differences. According to this embodiment, the parities B1F(1) to B3F(1), B1F(4) to B3F(4) (i=1,4) in the non-arranged direction and the parities C1F(16) to C3F(16), C1F(17) to C3F(17) (j=16,17) in the arranged direction in FIG. 10 (of the sample F) are different from the counterparts in FIG. 8 (of the standard sample E). If at least one of the parities B1F(i) to B3F(i) in a column or the parities C1F(j) to C3F(j) in a row is different from the counterpart, the parities in the column or the row are considered to be different from the counterparts as a whole, respectively.

Consequently, of all the partial data AF(i,j) in FIG. 10 (of the sample F), the four partial data AF(1,16), AF(4,16), AF(1,17), and AF(4,17), which are located in the points where the columns with i=1, 4 and the rows with j=16, 17 intersect, can be identified as being different from the counterparts in FIG. 8 (of the standard sample E). Furthermore, the partial data AF(i,j) of the sample F other than those different ones can be considered to be almost the same as the counterparts of the partial data A(i,j) of the standard sample E.

FIG. 11 shows mainly the parities B1F(1) to B3F(1), B1F(4) to B3F(4), C1F(16) to C3F(16), and C1F(17) to C3F(17) of the sample F in FIG. 10 differing from the counterparts in FIG. 8. The data X1, X2, Y1, and Y2 to be recovered are also indicated in FIG. 11 at the positions of partial data AF(1,16), AF(4,16), AF(1,17), and AF(4,17) differing from the counterparts in FIG. 8. These data X1, X2, Y1, and Y2 to be recovered are identical to the partial data A(1,16), A(4,16), A(1,17), and A(4,17), respectively, in FIG. 8 (the standard sample E).

In the next step 132, the information processor checks whether the number of the partial data (hereinafter referred to as "AF(i',j')"), which differ from the counterparts of the partial data A(i,j) in FIG. 8, of the partial data AF(i,j) in FIG. 10 is three at the most for each column and each row. If the result of the check is affirmative, the partial data of the standard sample E corresponding to the partial data AF(i',j')

can be computed (recovered) correctly by solving simultaneous equations on Galois field $GF(2^{128})$. In this embodiment, since the number of the partial data differing from the counterparts is two for 1stand 4th columns and two for 16th and 17th rows, the result of the check is affirmative. The procedure thus moves to step 133, and the information processor recovers the corresponding partial data A(i',j') (X1, X2, Y1, Y2) of the standard sample E in accordance with the flowchart of FIG. 12 using two sets of different parities and the partial data of the sample F differing from the counterparts. All the computations in FIG. 12 are carried out on Galois field $GF(2^{128})$.

In this case, since the number of the unknown numbers X1, X2 in the 16th row is two in FIG. 11, simultaneous first-degree equations with two variables are formed using two parities C1F(16), C2F(16) in the 16th row, the corresponding two parities C1(16), C2(16) in FIG. 8, and the partial data AF(1,16), AF(4,16) of the sample F corresponding to the unknown numbers X1, X2. That is, the equations for the parities C1(16) and C1F(16) reduce to equations (G1) and (G2) of step 141 in FIG. 12, and the equations for the parities C2(16) and C2F(16) reduce to equations (G3) and (G4) of step 142 using the primitive element α of equation (15).

Equations (G5) and (G6) of step 143 are then obtained by subtracting the equations (G2) and (G4) from the equations (G1) and (G3), respectively. The simultaneous first-degree equations with two variables are then obtained by assuming the right sides of the equations (G5) and (G6) to be C1X and C2X respectively. Then, the unknown numbers X1 and X2 can be expressed in equations (G7) of step 144 by solving the simultaneous equations. Actually solving the equations gives the values of X1 and X2 as follows (see FIG. 11). It should be noted that if the number of the unknown numbers is 3, simultaneous first-degree equations with three variables have only to be solved, for example, further using the third parities C3(16), C3F(16). If the number of the unknown is 1, the equations can be solved using only the first parities C1(16), C1F(16) and the like.

$$X1 = hex(43475447474347544347544354434154) \quad (27)$$

$$X2 = hex(47545447434147474743414747545454541) \quad (28)$$

In addition, these numerical data are converted to the sequences of characters as follows using a function chr( ) which converts a string of ASCII codes to a string of characters (see FIG. 11). In contrast to the above-mentioned function asc( ), the function chr( ) converts a string of ASCII codes to a string of characters one byte by one byte so that the most significant and the least significant ASCII codes are converted to characters placed at the end and front parts, respectively.

```
chr(X1) = TACTCTGCTGCGGTGC = T(1, 16) =      (29)
TF(1, 16)

chr(X2) = ATTTGGACGGACGTTG = T(4, 16)        (30)
```

Thus, it is understood that the partial text data T(1,16) of the standard sample E is the same as the partial text data TF(1,16) of the sample F, and only the partial text data T(4,16) is different from the partial text data TF(4,16) (see FIG. 9).

Then, regarding the unknown numbers Y1, Y2 in the 17th row in FIG. 11, simultaneous first-degree equations with two variables are formed using two parities C1F(17), C2F(17) in the 17th row, the corresponding two parities C1(17), C2(17) in FIG. 8, and the partial data AF(1,17), AF(4,17) of the sample F corresponding to the unknown numbers Y1, Y2. The simultaneous first-degree equations consist of equations (G8) and (G9) of step 145 in FIG. 12. Then, the unknown numbers Y1 and Y2 can be expressed in equations (G10) of step 146 by solving the simultaneous equations. Actually solving the equations gives the values of Y1 and Y2 as follows (see FIG. 11):

$$Y1 = hex(47544343415441544354474747474341), \quad (31)$$

$$Y2 = hex(41544343544475441147435444741414754). \quad (32)$$

These numerical data (a string of ASCII codes) are further converted to strings of characters as follows (see FIG. 11):

```
chr(Y1) = ACGGGGTCTATACCTG = T(1, 17),       (33)

chr(Y2) = TGAAGTCGATGTCCTA = T(4, 17) =      (34)
TF(4, 17).
```

Thus, it is understood that the partial text data T(4,17) of the standard sample E is the same as the partial text data TF(4,17) of the sample F, and only the partial text data T(1,17) is different from the partial text data TF(1,17) (see FIG. 9). According to the method of this embodiment, the unknown numbers X1, X2, Y1, and Y2, i.e. the partial data A(1,16), A(4,16), A(1,17), and A(4,17) of the standard sample E are recovered correctly. Here, since the partial data A(1,16) and A(4,17) are the same as the partial data AF(1, 16) and AF(4,17), respectively, those partial data need not be considered as the recovered data.

In the next step 134, after substituting the recovered partial data A(i',j'), i.e. A(4,16) and A(1,17) for the corresponding partial data AF(4,16) and AF(1,17) of the binary data BN2 of the sample F in FIG. 10, the information processor inversely converts the binary data BN2 obtained by the substitution into the text data TX1'. In addition, the information processor computes the 128-bit message digest AB1' of the text data TX1' by the MD5 hash function, and checks whether the message digest AB1' is equal to the message digest AB1 (which is recorded in the temporary file in step 121) of the standard sample E. In this embodiment, it holds true that AB1'=AB1. However, there is some possibility that the positions of the partial data AF(i,j) of the sample F in FIG. 10 differing from the counterparts cannot be detected correctly, depending on where and how the partial data differing from the counterparts are distributed. If this is the case and it holds true that AB1'≠AB1, the procedure only has to move to step 135. Since in usual cases it holds true that AB1'=AB1, the procedure moves to step 138, and the information processor records the information on "the positions (i',j') of the differences between the sequences of the sample F and the standard sample E and the pairs of the differing partial text data" in the above-mentioned first data file. In this embodiment, the positions (4,16) and (1,17) are recorded as the positions (i',j') and the partial text data A(4,16), AF(4,16), and A(1,17), AF(1,17) are recorded as the pairs of the differing partial text data.

On the other hand, in step 132, if the number of the partial data AF(i',j') differing from the counterparts is four or more at least for one column or one row, then the correct recovery of the partial data in the column or the row is difficult, respectively. The procedure thus moves to step 135, and the user purchases the complete data of the standard sample E, i.e. the binary data BN1 in FIG. 8 from the supplier of the DNA information through the communications network 1 (the Internet), and the information processor of the computer system 2B records the binary data BN1 in the third data file defined in the memory device.

Then, in step 136, the information processor inversely converts the binary data BN1 into the text data TX1', and computes the 128-bit message digest AB1' by applying the MD5 hash function to the text data TX1'. The information processor then checks whether the message digest AB1' is equal to the message digest AB1 of the standard sample E (which is recorded in the temporary file in step 121). In usual cases it holds true that AB1'=AB1, but if the binary data BN1 is not transmitted correctly because of communication errors, for example, it follows that AB1'≠AB1. In this case, for example, the information processor requests that the supplier transmit the complete data again. If it holds true that AB1'=AB1 in step 136, the procedure moves to step 137, and the information processor obtains the partial data A(i',j'), which correspond to the different partial data AF(i',j') of the sample F, of the binary data BN1 of the standard sample E. The procedure then moves to step 138.

In the above-mentioned step 135, the user purchases the complete data (the binary data BN1) from the supplier of DNA information. However, instead of the procedure in the step 135, the user may purchase only the partial data A(i',j'), which is identified in the step 131 and corresponds to the different partial data AF(i',j') of the standard sample E. This reduces the communications cost.

According to the business model of this embodiment of the invention, at the first stage, the parity information of the standard sample E (B1(i) to B3(i), C1(j) to C3(j)) is purchased. Then, the purchased parity information and the parity information of the sample F (B1F(i) to B3F(i), C1F(j) to C3F(j)) are compared. And, if the number of the different partial data AF(i,j) is small, the corresponding partial data A(i,j) of the standard sample E is recovered, while if the number of the different partial data is large, the complete data or only the different partial data is purchased. The user thus doesn't need to purchase a huge amount of the complete data at first, and the communications time can be shortened and the cost needed for information processing can be reduced.

Furthermore, by using the parity information of this embodiment of the invention, the error such as the SNP (Single Nucleotide Polymorphism) in which only one nucleotide (or base) differs from the counterpart within a certain range can be easily detected and correctly recovered.

In the above-stated embodiment, the user of the DNA information reads the sequences ST1, SB1, the message digest AB1, the sequences STR1, SBR1, and the message digest ABR1 of the standard sample E from the contents file in step 121. The user then checks whether the standard sample E and the sample F are the same in steps 122-128, and if the two samples are different, the user purchases the parity information of the standard sample E (the summary data). However, since it is reasonable that at least some parts of the sample F are usually different from the counterparts of the standard sample E, the user may omit the procedures from the acquisition of the message digest AB1, etc. to the check of the sameness of two samples. The user then may purchase the parity information of the standard sample E (the summary data) from the supplier of DNA information by directly performing the procedure of step 129.

In the above-stated embodiment, as shown in FIG. 8, the number of the first set of parity information (B1(i) to B3(i)) and the number of the second set of parity information (C1(j) to C3(j)) are the same. However, when the number (=4) of the partial data A(i,j) in the arranged direction is smaller than the number (=32) of the partial data A(i,j) in the non-arranged direction, the amount of the second set of parity information may be made less than that of the first set of parity information, for example, by using only C1(j), only C2(j), or only C1(j) and C2(j) as the parity information in the arranged direction. The amount of data of all the parity information can thus be reduced. In this case, any differences between the standard sample E and the sample F can be accurately detected, and the partial differences like the SNP can be accurately recovered.

Furthermore, when the number of the partial data placed in the arranged direction is smaller than that of the partial data placed in the non-arranged direction as shown in FIG. 8 (FIG. 7), the partial data A(i,j) and the parity information can be displayed on a monitor efficiently by letting the arranged direction of the partial data being parallel (horizontally) to the width of the monitor and scrolling the displayed information to the non-arranged direction. In this case, provided that the partial data A(i,j) is an m-bit quantity, the number of the partial data in the non-arranged direction is preferably smaller than or equal to $(2^{m}-1)/4$. Accordingly, since mutually different four parities can be computed as the parity information in the non-arranged direction, ordinary partial differences between two samples can be recovered correctly.

In the above-stated embodiment, the text data TX1 of the standard sample E in FIG. 7 is converted into the sequence of the partial data A(i,j) in FIG. 8 in step 105, where the size of the text data TX1 is the same of that of all the partial data, and the parity information is computed from the sequence. Instead of the procedure, in order to reduce the amount of data, the text data TX1 of the standard sample E in FIG. 7 may be converted into the binary data (numerical data) based on the Table 1 (a conversion table representing each nucleotide by two-bit data), where the size of the binary data is reduced to ¼ of that of the text data, and the binary data may be divided into the sequence of plural partial data placed in the arranged direction and in the non-arranged direction.

FIG. 13 shows the sequence of the 64-bit (8-byte) partial data B(i,j) (i=1 to 5, j=1 to 13) obtained like that and arranged in 5 columns in the arranged direction along which nucleotides are placed and in 13 rows in the non-arranged direction in hexadecimal notation. Each partial data B(i,j) in FIG. 13 corresponds to each sequence of consecutive 32 nucleotides of the standard sample E in FIG. 7. In the sequence, since the part of the standard sample E in FIG. 7 corresponding to the last partial data B(5,13) doesn't exist, the dummy data consisting of hex(000 . . . 000)) is added to the place of the partial data B(5,13).

Then, in the procedure corresponding to the step 106, a certain operation on Galois field $GF(2^{64})$ (m=64) is applied to the partial data B(i,j) by considering the partial data B(i,j) to be an element of Galois field $GF(2^{64})$ in vector representation. The following polynomials are used as an irreducible polynomial GF(X) and a primitive element α on Galois field $GF(2^{64})$.

$$GF(X)=1+X^{5}+X^{23}+X^{43}+X^{64} \qquad (35)$$

$$\alpha=X \qquad (36)$$

Moreover, the following irreducible polynomial GF'(X) can also be used, for example, as another irreducible polynomial on Galois field $GF(2^{64})$, and the following element α' can be used as a primitive element corresponding to the irreducible polynomial GF'(X).

$$GF'(X)=1+X^{7}+X^{62}+X^{63}+X^{64} \qquad (35A)$$

$$\alpha'=1+X \qquad (36A)$$

The information processor 10 in FIG. 10 then computes the first parity B1B(i), the second parity B2B(i), and the third parity B3B(i) for the partial data B(i,j) of each column (i=1 to 5) shown in FIG. 13 by adding up all the partial data B(i,j), calculating the sum $\Sigma\alpha^{(j-1)}\cdot B(i,j)$, and calculating the sum $\Sigma\alpha^{2(j-1)}\cdot B(i,j)$, respectively, along the non-arranged direction (j=1 to 13) of each column on Galois field GF($2^{64}$). These calculations correspond to equations (19) to (21), and each of the first set of parity information (B1B(i) to B3B(i)) is a 64-bit quantity.

In addition, the information processor 10 computes the first parity C1B(j), the second parity C2B(j), and the third parity C3B(j) for the partial data B(i,j) of each row (j=1 to 13) shown in FIG. 13 by adding up all the partial data B(i,j), calculating the sum $\Sigma\alpha^{(i-1)}\cdot B(i,j)$, and calculating the sum $\Sigma\alpha^{2(i-1)}\cdot B(i,j)$, respectively, along the arranged direction (i=1 to 5) of each row on Galois field GF($2^{64}$). These calculations correspond to equations (22) to (24), and each of the second set of parity information (C1B(j) to C3B(j)) is a 64-bit quantity.

In this case, the amount of data of the two sets of parity information (B1B(i) to B3B(i), C1B(j) to C3B(j)) can be reduced to almost ¼ of that of the parity information (B1(i) to B3(i), C1(j) to C3(j)) in FIG. 8. Thus, the parity information can be transmitted in a short time through the communications network and the information can be recorded in mediums whose memory capacity is relatively small.

In this case, when the user computes the parity information of the sample F in FIG. 9, the user has only to convert the text data of the sample F to the partial data based on the Table 1, where the size of all the partial data is reduced to ¼ of that of the text data, and compute the first and second sets of parity information by performing the operations on Galois field GF($2^{64}$). Then, the detection of the positions of the different data and the recovery of the data of the standard sample can be carried out in a similar manner to the above-stated embodiment.

In the above-stated embodiment, since there are four kinds of nucleotides constituting DNA or RNA, when the text data TX1 is converted into the reduced binary data, each nucleotide is represented by two-bit data as shown in Table 1. On the other hand, in some applications the following 16 kinds of characters a-n (8-bit ASCII code) are used as the text data showing each nucleotide (or base).

TABLE 2

| | |
|---|---|
| A | adenine (this indicates the nucleotide including adenine, and so forth) |
| c | cytosine |
| g | guanine |
| t | thymine |
| u | uracil |
| m | adenine or cytosine |
| r | guanine or adenine |
| w | adenine or thymine (or uracil) |
| s | guanine or cytosine |
| y | thymine (or uracil) or cytosine |
| k | guanine or thymine (or uracil) |
| v | adenine, guanine, or cytosine |
| h | adenine, cytosine, or thymine (or uracil) |
| d | adenine, guanine, or thymine (or uracil) |
| b | guanine, cytosine, or thymine (or uracil) |
| n | (adenine, cytosine, guanine, or thymine (or uracil)) or (unknown or other base) |

In this case, these 16 kinds of characters may be converted into mutually different four-bit codes, and then the text data may be converted into the numerical data (binary data) using the four-bit codes. This conversion reduces the amount of data by half. Furthermore, if the kinds of nucleotides (bases) increase in the future, the nucleotides may be expressed as the data of five or six bits.

Although in the above-mentioned embodiment the messages digests are computed by applying the hash function to the text data showing the nucleotide sequences in FIGS. 7 and 9, those text data are equivalent to the binary data (numerical data) converted based on Table 1, for example, in terms of the amount of the sequence information. Therefore, the message digests may be computed by applying the hash function to the binary data so as to be compared. Since the size of the binary data is nearly one-fourth of the size of the text data, the computation time for the message digest can be shortened.

In the above-stated embodiment, the information on the sequences of nucleotides (or the sequences of bases) constituting DNA or RNA is processed. However, the present invention can also be applied to the cases in which the information on sequences of nucleotides constituting genes is processed.

Another embodiment of the present invention will be described next with reference to the accompanying drawings. In this embodiment of the invention, some pieces of information on sequences of amino acids (biological compounds) in proteins or peptides are processed with computer systems.

In this embodiment, the computer system 2A shown in FIG. 1 can also be used basically, except that a protein sequencer is connected to the information processor 10 as the sequencer for reading amino acid sequences in proteins instead of the sequencer 4 for DNA. It should be noted that databases of amino acid sequences can also be used as the protein sequencer. In this embodiment, suppose that the sequence of amino acids in the protein of the newly discovered sample G, for example, is read by the sequencer, and the text data (hereinafter referred to as "TX3") showing the sequence is supplied to the information processor 10. The size of the text data corresponding to the sequence of n amino acids is n bytes, provided that one-Letter Code is used. In this embodiment, the sample G is supposed to be *E. coli*, whose sequence data was obtained from the above-mentioned website 1. The text data showing the sequence of a series of 820 amino acids in a certain protein of *E. coli* is used as the text data TX3 as shown in FIG. 14.

The sequence of a series of amino acids in the sample G is shown in SEQ ID NO:3 in Sequence Listing. The text data shown in FIG. 14 was generated by removing all numerical data from the sequence in SEQ ID NO:3 and expressing the sequence in one-Letter Code. Referring to FIG. 14, the text data is divided into plural 4-character partial text data arranged in 8 columns in the arranged direction (corresponding to the direction along which amino acids are placed) and in 26 rows in the non-arranged direction normal to the arranged direction, and a series of dummy "0" are temporarily written in the positions of data showing the 821st and later amino acids (this part is not included in the text data TX3 to be exact).

The information processor 10 then computes the 128-bit message digest AB3 by applying the MD5 hash function to the supplied text data TX3, and obtains the number NA3 of amino acids in the sequence and two sequences ST3 and SB3 of 8 amino acids taken respectively from the top and end portions of the text data TX3 as follows:

$$AB3=\text{hex}(0f66dc2b3024a9739d0e912fde12b8ba), \tag{41}$$

NA3=820,

ST3=MRVLKFGG, SB3=TLSWKLGV.

The information processor 10 then obtains the text data TXR3(=VGLKWS . . . FKLVRM) by rearranging the text data TX3 in reverse order. In addition, the information processor 10 obtains the message digest ABR3 by applying the MD5 hash function to the text data TXR3, and obtains two sequences STR3 and SBR3 of 8 amino acids corresponding respectively to the top and end portions of the text data TXR3. The sequences STR3 and SBR3 are easily obtained by rearranging the sequences SB3 and ST3 in reverse order. These values are as follows. It may be said that the sequence of the text data TXR3 is related to that of the original text data TX3 in such a way that they are palindromes to each other.

$$ABR3=\text{hex}(e895f433e1e77f84b3cadeead1a52380) \tag{42}$$

STR3=VGLKWSLT, SBR3=GGFKLVRM

The information processor 10 subsequently records the information on the name of the sample G (the information identifying the sample), the number NA3, the text data TX3, the sequences ST3 and SB3, the message digest AB3, the reversed sequences STR3 and SBR3, and the message digest ABR3 of the reversed sequence in the master file 19 defined in the magnetic disk unit 17. In this procedure, provided that the master file 19 is divided into two or more files, the text data TX3 and other data may be recorded in different files. The information processor 10 then divides the text data TX3 of the sample G into partial text data TG(i,j) with eight characters (64-bit data) arranged in N columns in the arranged direction (corresponding to the direction along which amino acids are placed) and in M rows in the non-arranged direction normal to the arranged direction as shown in FIG. 14 the same as in FIG. 7, for example. N and M are arbitrary integers of two or more respectively. In this embodiment, the text data TX3' of 832(=8·4·26) bytes is obtained by adding the dummy data of 12 characters (for example the character "A" may be used as well as the number "0" of this embodiment) to the text data TX3, and the text data TX3' is divided such that N=4 and M=26.

In this embodiment, each of the partial text data TG(i,j) with 8 characters is treated as just the 64-bit partial data AG(i,j) using the function asc( ) which simply converts the text data into the ASCII codes (numerical data) as follows:

$$AG(i,j)=\text{asc}(TG(i,j)). \tag{43}$$

It should be noted that the function asc(TG(i,j)) converts the partial text data TG(i,j) in reversed order so that the codes of the characters at the front and end of the partial text data are placed in the least and most significant parts, respectively, as shown by the converted example of TG(3, 11) in FIG. 14. In this case, it is possible to express each amino acid as 6-bit data. However, since the amount of data is reduced to only about ¾ of that of the ASCII-code expression, the partial text data (a string of ASCII codes) is used simply as the partial data (numerical data) in this embodiment.

FIG. 15 shows the sequence of the partial data AG(i,j) of the sample G. Then, in the same way as the example of FIG. 13, the information processor 10 applies a certain operation on Galois field GF($2^{64}$) (m=64) to the partial data AG(i,j) by considering the 64-bit partial data AG(i,j) arranged in 4 columns and 26 rows in FIG. 15 to be elements of Galois field GF($2^{64}$) in vector representation. The polynomials defined by equation (35) (or (35A)) and equation (36) (or (36A)) are used as an irreducible polynomial GF(X) and a primitive element α on Galois field GF($2^{64}$), respectively.

More specifically, the information processor 10 computes the first parity B1G(i), the second parity B2G(i), and the third parity B3G(i) for the partial data AG(i,j) of each column (i=1 to 4) shown in FIG. 15 by adding up all the partial data AG(i,j), calculating the sum $\Sigma\alpha^{(j-1)}\cdot AG(i,j)$, and calculating the sum $\Sigma\alpha^{2(j-1)}\cdot AG(i,j)$, respectively, along the non-arranged direction (j=1 to 26) of each column on Galois field GF($2^{64}$). These calculations correspond to equations (19) to (21), and each of the first set of parity information (B1G(i) to B3G(i)) is a 64-bit quantity.

The information processor 10 then computes the first parity C1G(j), the second parity C2G(j), and the third parity C3G(j) for the partial data AG(i,j) of each row (j=1 to 26) shown in FIG. 15 by adding up all the partial data AG(i,j), calculating the sum $\Sigma\alpha^{(i-1)}\cdot AG(i,j)$, and calculating the sum $\Sigma\alpha^{2(i-1)}\cdot AG(i,j)$, respectively, along the arranged direction (i=1 to 4) of each row on Galois field GF($2^{64}$). These calculations correspond to equations (22) to (24), and each of the first set of parity information (C1G(j) to C3G(j)) is a 64-bit quantity. The parities B1G(i) to B3G(i), C1G(j) to C3G(j) computed in this way are expressed in FIG. 15 in hexadecimal notation.

In this embodiment, three parities are computed for each column and each row. However, since the amount of data of an amino acid sequence is much less than that of a nucleotide sequence, only one parity (for example, B2G(i) and C2G(j)) may be used for each column (in the non-arranged direction) and for each row (in the arranged direction) as the parity information for practical use. In the embodiment of FIG. 15, suppose that only the parities B2G(i) and C2G(j) are used, then since each parity is a 64-bit (8-byte) quantity, the data of all parities adds up to 240(=8·30) bytes. The data of all parities is thus reduced to nearly ⅓ of that of the original text data TX3 (820 bytes).

Then, the information processor 10 records the information on the sample G's name, the number NA3, the text data TX3, the message digests AB3, ABR3, and the parity information in the working file 20 defined in the magnetic disk unit 17. The working file 20 may be divided into two or more files. The information processor 10 then records the information on the sample G's name, the number NA3, the sequences ST3, SB3, the message digest AB3, the reversed sequences STR3, SBR3, and the message digest ABR3 of the reversed sequence in the contents file 21 defined in the magnetic disk unit 17. Besides, the information processor 10 transmits the information on the data in the contents file 21 to the contents provider 3 through the communications network 1, thereby enabling the data in the contents file 21 to be recorded in the contents file 31 defined in the server of the provider 3 and accessible freely. This means that the data in the contents file 21 is disclosed to the public through the Internet. Accordingly, a third party can check whether the sample G is novel to them by comparing the number NA3 and the message digest AB3 (or ABR3, if necessary) disclosed to them respectively with the number of amino acids in the sequence of the sample owned by them and the message digest of the sequence of the sample. In addition, users can avoids purchasing the same sequence information on the sample G from two or more suppliers by mistake.

Subsequently, the owner of the computer system 2A (the supplier of amino acid information) enters the state to wait for purchase orders from users. When a user sends a purchase order for the summary data of the sample G, the information processor 10 transmits the parity information (for example, B2G(i), C2G(j)) of the sample G in the working file 20 defined in the magnetic disk unit 17 to the user as an email attachment. The user who purchased the parity information compares the parities of the amino acid sequence of the sample, which is of the same kind as the sample G and which sequence was deciphered by themselves, with the purchased parities, and thus can detect and recover the differences between the two sequences to some extent.

On the other hand, when a user sends a purchase order for the complete data, the information processor 10 compresses the text data TX3 in the working file 20 into the data such as a ZIP file and the like, and transmits the compressed data to the user as an email attachment, for example. In this case, the information processor 10 may transmit the message digest AB3 computed by the hash function as well, if necessary. According to this embodiment, since the size of the summary data (the parities) can be reduced, the summary data can be transmitted in a short time.

In addition, the supplier of the sequence information on amino acids may record the information stored in the working file 20, i.e. the information on the sample G's name, the number NA3, the text data TX3, the message digests AB3, ABR3, and the parity information in the CD-R 16 by way of the CD-R/RW drive 15. The CD-R 16 may be reproduced on more CD-ROMs, and these recording mediums may be sold to users by mail and the like.

In the above-stated embodiment, the text data corresponding to the sequence of biological compounds or the numerical data obtained by converting the text data based on a conversion rule is divided into plural m-bit partial data arranged in plural columns in the arranged direction, along which the biological compounds are placed, and in plural rows in the non-arranged direction which crosses the arranged direction, where m is an integer larger than or equal to 16. A first set of parity information are then computed by applying a first operation of Galois field $GF(2^m)$ along the non-arranged direction to the partial data of each column. A second set of parity information are then computed by applying a second operation of Galois field $GF(2^m)$ along the arranged direction to the partial data of each row.

Regarding the procedures, if m is smaller than 16, each partial data corresponds to the sequence of from 1 to 7 nucleotides or from 1 to 2 amino acids, for example. Therefore, there is the inconvenience of having to compute too many pieces of parity information for a sequence of the biological compounds. In addition, we cannot make the most of computational abilities of resent computers. Especially, when the processing unit of computers is a multiple of 64 bits, the value of m may be preferably a multiple of 64 such as 64, 128, 192, 256, etc. in order to compute the parity information efficiently.

Moreover, in the embodiment of FIG. 13, provided that the prime number larger than m-bit number is denoted by P ($P>2^m$), it is possible to compute the parity information on Galois field $GF(P)$, in which operations are performed mod P. However, since some pieces of the parity information obtained by applying operations to the m-bit partial data on Galois field $GF(P)$ exceed m-bit numbers, there is the inconvenience of having the total parity information whose size is $(m+1)/m$ times the size of that obtained using Galois field $GF(2^m)$. That is, one advantage of Galois field $GF(P)$ is its easy operations, while one advantage of Galois field $GF(2^m)$ is its compact parity information, because every piece of the parity information is expressed as an m-bit number on Galois field $GF(2^m)$.

In order to seek a large prime number P larger than $2^m (m>16)$ or slightly smaller than $2^m$, for example, the Miller-Rabin's method for testing primality (see, for example, the reference (M. O. Rabin: "Probabilistic algorithms for testing primality", Journal of Number Theory, 12, pp. 128-138 (1980))) can be used. Furthermore, in order to factorize a large number for seeking a primitive element, for example, the quadratic sieve method (see, for example, the reference (C. Pomerance: "Factoring", In Cryptology and Computational Number Theory, pp. 27-47, American Mathematical Society (1990))) can be used. In addition, a practical method of determining a large prime number P and factorizing a large number is to use the built-in function "ECM" in the above-mentioned "UBASIC".

Galois field $GF(P)$, where P is a prime number, consists of P elements $(0, 1, \ldots, P-1)$, and the operations of addition, subtraction, multiplication, and division are carried out mod P on Galois field $GF(P)$. In order to apply Galois field $GF(P)$ to the above-stated embodiment of the invention, each of the m-bit partial data $A(i,j)$ has only to be expressed as any element of Galois field $GF(P)$. In order to computes the parity information easily, a primitive element $\delta$ of Galois field $GF(P)$ may be used. Provided that $k=P-1$, the primitive element $\delta$ of Galois field $GF(P)$ satisfies the following relations modulo P:

$$\delta^k = 1 \pmod{P}, \tag{A2}$$

$$\delta^{k'} \neq 1 \pmod{P} (1 \leq k' < k). \tag{A3}$$

Suppose that the integer k can be factorized as follows using prime numbers p1, p2, ..., pr and integers n1, n2, ..., nr:

$$k = P - 1 = p1^{n1} \cdot p2^{n2} \ldots pr^{nr}. \tag{A4}$$

Then, the primitive element $\delta$ is determined so that all of $\delta$ to the power of $(p1^{n1-1} \cdot p2^{n2} \ldots pr^{nr})$, $\delta$ to the power of $(p1^{n1} \cdot p2^{n2-1} \ldots pr^{nr})$, ..., and $\delta$ to the power of $(p1^{n1} \cdot p2^{n2} \ldots pr^{nr-1})$ do not come to 1 mod P.

Moreover, since an arbitrary nonzero element $\epsilon$ of Galois field $GF(P)$ satisfies equation (A2), the inverse element $\epsilon^{-1}$ of $\epsilon$ can be computed as follows by the use of $k(=P-1)$:

$$\epsilon^{-1} = \epsilon^{k-1} \pmod{P}. \tag{A5}$$

Therefore, for example, when the partial data is divided by $\epsilon$, we have only to multiply the partial data by $\epsilon^{k-1}$.

Then, when Galois field $GF(P)$ is used, the procedures of the supplier and user of DNA information shown in FIGS. 3 to 6 can be carried out by substituting the operations on Galois field $GF(P)$ for the operations on Galois field $GF(2^m)$.

More specifically, when the parity information is computed on Galois field $GF(P)$ in the embodiment in FIG. 13 (for example, the standard sample), a prime number (for example, the smallest one) that is larger than $2^{64}(m=64)$ and smaller than or equal to $65(=m+1)$-bit numbers may be used as the prime number PF because it is possible that the partial data $B(i,j)$ will take all 64-bit values. The prime number P of this kind is as follows in hexadecimal notation. In addition, for example, the following number may be used as a primitive element $\delta$ corresponding to the prime number P. In this case, since 3 is also a primitive element, if a number except 2 to the power of any number is preferable as a primitive element, for example, 3 may be used as the primitive element $\delta$.

$$P = \text{hex}(100000000000000d) \tag{A6}$$

$$\delta = 2 \tag{A7}$$

In the procedure corresponding to step 106 under these conditions, each 64-bit partial data $B(i,j)$ is performed certain operations on Galois field $GF(P)$ using the primitive element $\delta$ by considering the partial data $B(i,j)$ to be an element of Galois field $GF(P)$. For example, the first parity $B1B(i)'$, the second parity $B2B(i)'$, and the third parity $B3B(i)'$ for the partial data $B(i,j)$ of each column $(i=1$ to 5$)$ shown in FIG. 13 are computed by adding up all the partial data B(i,j), calculating the sum $\Sigma\delta^{(j-1)} \cdot B(i,j)$, and calculating the sum $\Sigma\delta^{2(j-1)} \cdot B(i,j)$, respectively, along the non-arranged direction (j=1 to 13) of each column on Galois field GF(P). These calculations correspond to equations (19) to (21), and each of the first set of parity information (B1B(i)' to B3B(i)') is a (64+1)-bit quantity at the most.

In addition, the first parity C1B(j)', the second parity C2B(j)', and the third parity C3B(j)' for the partial data B(i,j) of each row (j=1 to 13) shown in FIG. 13 are computed by adding up all the partial data B(i,j), calculating the sum $\Sigma\delta^{(i-1)} \cdot B(i,j)$, and calculating the sum $\Sigma\delta^{2(i-1)} \cdot B(i,j)$, respectively, along the arranged direction (i=1 to 5) of each row on Galois field GF(P). These calculations correspond to equations (22) to (24), and each of the second set of parity information (C1B(j)' to C3B(j)') is also a (64+1)-bit quantity at the most.

Furthermore, in the procedure corresponding to step 130, the first and second sets of parity information are computed on Galois field GF(P) in the non-arranged and arranged directions, respectively, for the partial data sequence of the sample under inspection. Then, in the procedures of this embodiment corresponding to steps 131-138, the comparison between the parity information of two samples, the detection of the different partial data, and the recovery of the different data can be carried out.

Then, provided that the partial data takes all 128-bit values (m=128), in order to compute the parity information for the partial data on Galois field GF(P), the following prime number may be used as a prime number P lager than $2^{128}$ and smaller than or equal to 129-bit number. And, the following number may be used as a primitive element $\delta$ corresponding to the prime number P.

$$P=2^{128}+51 \tag{A8}$$

$$\delta=2 \tag{A9}$$

On the other hand, when the text data itself is used as the partial data A(i,j) like the embodiments of FIGS. 7 and 8, the maximum value Nmax of the m-bit partial data A(i,j) is smaller than $(2^{m}-1)$. More specifically, suppose that ASCII codes are used as the text data in FIG. 7, since the ASCII codes of the alphabets are hex(41) to hex(7a), the maximum value Nmax is as follows:

$$N\text{max}=\text{hex}(7a7a7a7a \ldots 7a7a7a)<2^{m}-1. \tag{A10}$$

In this case, the prime number P defining the Galois field GF(P) can be selected so that it is not only larger than the maximum value Nmax of the partial data A(i,j) but it is also an m-bit number as follows:

$$2^{m}>P>N\text{max}. \tag{A11}$$

Furthermore, when m=128 and the equation (A10) holds good, the smallest prime number P that satisfies the equation (A11) and a primitive element $\delta$ corresponding to it are as follows:

$$P=\text{hex}(7a7a7a7a7a7a7a7a7a7a7a7a7a7a7a7f), \tag{A12}$$

$$\delta=5. \tag{A13}$$

When the first and second sets of parity information of the partial data A(i,j) in FIGS. 7 and 8 are computed on Galois field GF(P) using this prime number P and this primitive element $\delta$, each parity computed in this way is an m-bit quantity. Thus, according to this method, the operations are simple and the compact parity information whose size is the same as that computed on Galois field $GF(2^m)$ is obtained.

Similarly, when ASCII codes are used as the text data in the embodiment in FIGS. 14 and 15, the maximum value Nmax of the m-bit partial data AG(i,j) (m=64 in the case of FIG. 14) is as follows:

$$N\text{max}=\text{hex}(7a7a7a7a7a7a7a7a)<2^{m}-1. \tag{A14}$$

In this case, the prime number P defining the Galois field GF(P) can also be selected so that the equation (A11) is satisfied.

More specifically, when m=64 and the equation (A14) holds good, the smallest prime number P that satisfies the equation (A11) and a primitive element $\delta$ corresponding to it are as follows. In this case, since 5 is also a primitive element, for example, if a number except 2 to the power of any number is preferable as a primitive element, 5 and the like may be used as the primitive element $\delta$.

$$P=\text{hex}(7a7a7a7a7a7a7ad5) \tag{A15}$$

$$\delta=2 \tag{A16}$$

Furthermore, when the parity information is computed on Galois field GF(P), the number of the partial data placed in the arranged direction may be made smaller than that of the partial data placed in the non-arranged direction, and the number of the second set of parity information in the arranged direction may be made smaller than that of the first set of parity information in the non-arranged direction. Accordingly, the parity information can be easily displayed on a monitor, and the total amount of data of the parity information is kept from growing too much. In this case, in order to recover up to four different data in the non-arranged direction correctly using the primitive element $\delta$, the number of the partial data in the non-arranged direction has only to be made smaller than or equal to (P−1)/4.

In the above-stated embodiments, the parity information is computed by multiplying each partial data by a certain coefficient. However, for example, we may use the BCH codes (Bose-Chaudhari-Hocquenghem Codes) (see, for example, reference (J. L. Massey: "Shift Register Synthesis and BCH Decoding," IEEE Trans., IT-15, pp. 122-127 (1969))) as the parity information. It should be noted that the conventional BCH codes are constructed on Galois field $GF(2^{m'})$, where m' is a small number maybe smaller than or equal to 16. Thus, in order to apply the BCH codes to the present invention, the BCH codes have to be reconstructed on Galois field $GF(2^m)$, where m is a large number larger than or equal to 16 as is the case with the present invention.

Here, the hash function used in the above-stated embodiments will be described in more detail. The conventional hash function used in cryptography processes all codes including space code, linefeed code (return code), etc. in the text data. As for the sequence information on nucleotides and amino acids, as shown in SEQ ID NO:1 to 3 in Sequence Listing, space codes, numerical codes showing the order of the sequence, and linefeed codes are sometimes inserted in the text data so that the sequence is easy to read. Therefore, the hash function used for processing the sequence information on biological compounds such as nucleotides and amino acids may preferably have the function to leave out (disregard) the predetermined codes such as numerical codes, space code, and linefeed code. In addition, when one or more hyphen codes "-" are inserted between the adjacent characters (letters), the hash function needs to further leave out the hyphen codes. Furthermore, if "a kind of termination code" is added at the end of a file, the hash function may leave out such code.

In addition, if the sequences of nucleotides are usually written, for example, in lower-case letters, the hash function may compute the message digest after converting upper-case letters, which are unusually used, to lower-case letters selectively. On the contrary, if the sequences of amino acids are usually written, for example, in upper-case letters, the hash function may compute the message digest after converting lower-case letters, which are unusually used, to upper-case letters selectively.

In addition, when the original file is divided into two or more partial files, it might be sometimes preferable to add data (hereinafter referred to as "comment data") showing the order of division of the partial files and the like to each partial file. When the comment data is added to each partial file or one original file, the hash function needs to leave out the comment data. In order to leave out the comment data, for example, after recording the comment data between a certain start symbol (for example, /*) and a certain end symbol (for example, */), the hash function has only to leave out the data from the start symbol to the end symbol.

Furthermore, according to the above-mentioned embodiment, the partial sequences of the first and end parts of the nucleotide sequence in the DNA of an organism (or the amino acid sequence in a protein) and the message digest of the text data showing the sequence are sometimes disclosed on the Internet. In this case, there is a possibility that the text data is recovered from the disclosed partial sequences and the message digest. When the message digest of the text data is computed, the hash function may be performed on the remainder that is left after removing the partial sequences from the text data in order to avoid the recovery.

Then, in the step 124 in FIG. 5 of the above-stated embodiment, if the number NA2 of the sample F's sequence differs from the number NA1 of the standard sample E's sequence by k (k is an integer larger than or equal to 1) and, for example, NA2=NA1+k, the data corresponding to k nucleotides may be removed from the text data TX2 of the sample F, and then the procedure may move to step 126 to search for the differences. On the contrary, if it stands up that NA2=NA1−k, the dummy data corresponding to k nucleotides may be added to the text data, and then the procedure may move to step 126. Accordingly, the positions of the excesses or deficits of the sample F's sequence can be identified. In this case, if k=1, the position in the text data TX2, from which the excess data is removed or to which the dummy data is added, may preferably be at first a position dividing the total sequence half-and-half, then a position dividing the first or second half of the sequence half-and-half, then a position dividing the first or second half of the divided sequence, and so on. Accordingly, the position of the excess or deficit can be identified in the shortest time.

The present invention has been described above with respect to various preferred embodiments. However, the present invention is not limited to these embodiments. Various changes or modifications may be made within the scope of the present invention.

INDUSTRIAL APPLICABILITY

According to the present invention, the sequence information on biological compounds such as nucleotides in nucleic acids or genes and amino acids in proteins or peptides can be approximately represented by the parity information. The parity information can then be recorded in less amounts of data than the text data expressing the sequence. Therefore, the parity information can be recorded in mediums whose memory capacity are small and can be transmitted through a communications network in a short time. In addition, by performing operations on Galois field $GF(2^m)$, each parity information can be recorded concisely in the same amount of data as the m-bit partial data.

On the other hand, when the operations are performed on Galois field GF(P), where P is a prime number, in order to compute the parity information, the size of the parity information increases to (m+1)/m times that computed on Galois field $GF(2^m)$, while the operations are simplified.

Especially, when the maximum value Nmax of the partial data is smaller than $(2^{m}-1)$ and the prime number P can be selected so that the relation $(2^m > P > Nmax)$ is satisfied, the operations are simple and each piece of parity information can be recorded concisely in the same amount of data as the m-bit partial data.

Furthermore, the differences between two sequences of biological compounds can be easily identified (detected) by comparing two sets of parity information of the two sequences. And, the differences can be recovered, if necessary. Accordingly, the SNP (Single Nucleotide Polymorphism) can be easily detected by comparing two pieces of small amounts of data.

Furthermore, according to the present invention, a business model is provided, in which the parity information that approximately represents the sequence information on biological compounds such as nucleotides and amino acids can be supplied to uses in small amounts of data. In this case, by further using the mathematical digest, the user can easily check whether the purchased sequence information and the sequence information owned by the supplier are equal. In addition, the user can avoid purchasing the same sequence information from different suppliers by mistake.

The invention claimed is:

1. Device for recording sequence information on biological compounds, comprising:

a sequencer for reading sequence information on said biological compounds;

dividing means for dividing one of text data representing a sequence of said biological compounds and numerical data obtained by converting said text data utilizing a conversion rule, into a plurality of m-bit partial data arranged in a plurality of columns in an arranged direction corresponding to a direction along which said biological compounds are placed, and in a plurality of rows in a non-arranged direction which crosses said arranged direction, where m is an integer greater than or equal to 16;

computing means for computing a first set of parity information by applying a first operation of a Galois field GF($2^m$) along said non-arranged direction to a set of said partial data of each column and computing a second set of parity information by applying a second operation of a Galois field GF($2^m$) along said arranged direction to a set of said partial data of each row; and recording means for recording said first and second sets of parity information in a recording medium, wherein:

when $\alpha$ is a primitive element of a Galois field GF($2^m$), said first set of parity information includes a sum of a plurality of products obtained by multiplying a set of said partial data of each column along said non-arranged direction by $\alpha^{sp}$, $\alpha^{s(p+1)}$, $\alpha^{s(P+2)}$, ..., $\alpha^{s(p+dp)}$, where s and p are nonnegative integers and dp is an integer greater than or equal to one; and said second set of parity information includes a sum of a plurality of products obtained by multiplying a set of said partial data of each row along said arranged direction by $\alpha^{tq}$, $\alpha^{t(q+1)}$, $\alpha^{t(q+2)}$, ..., $\alpha^{t(q+dq)}$, where t and q are nonnegative integers and dq is an integer greater than or equal to one.

2. Method of utilizing sequence information on biological compounds, comprising:

recording one of text data representing a sequence of said biological compounds and numerical data obtained by converting said text data utilizing a conversion rule, in a first file;

dividing said one of text data and numerical data recorded in said first file into a plurality of m-bit partial data arranged in a plurality of columns in an arranged direction corresponding to a direction along which said biological compounds are placed, and in a plurality of rows in a non-arranged direction which crosses said arranged direction, where m is an integer greater than or eaual to 16;

computing a first set of parity information by applying a first operation of a Galois field GF($2^m$) along said non-arranged direction to a set of said partial data of each column, and computing a second set of parity information by applying a second operation of a Galois field GF($2^m$) along said arranged direction to a set of said partial data of each row;

recording said first and second sets of parity information in a second file;

receiving through a communications network from a supplier said first and second sets of parity information recorded on said second file;

identifying differences between said sequence of said biological compounds held by said supplier and a sequence of biological compounds subject to examination, based on said two sets of received parity information; and when said differences cannot be recovered, receiving sequence information on a part corresponding to said differences, within said one of text data and numerical data recorded in said first file, through said communications network from said supplier, wherein;

when $\alpha$ is a primitive element of a Galois field GF($2^m$), said first set of parity information includes a sum of a plurality of products obtained by multiplying a set of said partial data of each column along said non-arranged direction by $\alpha^{sp}$, $\alpha^{s(p+1)}$, $\alpha^{s(p+2)}$, ..., $\alpha^{s(p+dp)}$, where s and p are nonnegative integers and dp is an integer greater than or equal to one; and said second set of parity information includes a sum of a plurality of products obtained by multiplying a set of said partial data of each row along said arranged direction by $\alpha^{tq}$, $\alpha^{t(q+1)}$, $\alpha^{t(q+2)}$, ..., $\alpha^{t(q+dq)}$, where t and q are nonnegative integers and dq is an integer greater than or equal to one.

* * * * *

SEQUENCE LISTING

<160> NUMBER OF SEQ ID NOS: 3

<210> SEQ ID NO 1
<211> LENGTH: 2048
<212> TYPE: DNA
<213> ORGANISM: Escherichia coli

<400> SEQUENCE: 1
agcttttcat tctgactgca acgggcaata tgtctctgtg tggattaaaa aaagagtgtc    60

-continued

```
tgatagcagc ttctgaactg gttacctgcc gtgagtaaat taaaatttta ttgacttagg      120
tcactaaata ctttaaccaa tataggcata gcgcacagac agataaaaat tacagagtac      180
acaacatcca tgaaacgcat tagcaccacc attaccacca ccatcaccat taccacaggt      240
aacggtgcgg gctgacgcgt acaggaaaca cagaaaaaag cccgcacctg acagtgcggg      300 ctttttttt cgaccaaagg taacgaggta acaaccatgc gagtgttgaa gttcggcgt      360 acatcagtgg caaatgcaga acgttttctg cgtgttgccg atattctgga aagcaatgcc      420
aggcaggggc aggtggccac cgtcctctct gcccccgcca aaatcaccaa ccacctggtg      480
gcgatgattg aaaaaaccat tagcggccag gatgctttac ccaatatcag cgatgccgaa      540 cgtattttg ccgaactttt gacgggactc gccgccgccc agccggggtt cccgctggcg      600
caattgaaaa ctttcgtcga tcaggaattt gcccaaataa aacatgtcct gcatggcatt      660
agtttgttgg ggcagtgccc ggatagcatc aacgctgcgc tgatttgccg tggcgagaaa      720
atgtcgatcg ccattatggc cggcgtatta gaagcgcgcg tcacaacgt tactgttatc      780 gatccggtcg aaaaactgct ggcagtgggg cattacctcg aatctaccgt cgatattgct      840
gagtccaccc gccgtattgc ggcaagccgc attccggctg atcacatggt gctgatggca      900
ggtttcaccg ccggtaatga aaaggcgaa ctggtggtgc ttggacgcaa cggttccgac      960
tactctgctg cggtgctggc tgcctgttta cgcgccgatt gttgcgagat ttggacggac     1020
gttgacgggg tctatacctg cgacccgcgt caggtgcccg atgcgaggtt gttgaagtcg     1080
atgtcctacc aggaagcgat ggagctttcc tacttcggcg ctaaagttct tcaccccgc     1140 accattaccc ccatcgccca gttccagatc ccttgcctga ttaaaaatac cggaaatcct     1200
caagcaccag gtacgctcat tggtgccagc cgtgatgaag acgaattacc ggtcaagggc     1260
atttccaatc tgaataacat ggcaatgttc agcgtttctg gtccggggat gaaagggatg     1320
gtcggcatgg cggcgcgcgt ctttgcagcg atgtcacgcg cccgtatttc cgtggtgctg     1380
attacgcaat catcttccga atacagcatc agtttctgcg ttccacaaag cgactgtgtg     1440
cgagctgaac gggcaatgca ggaagagttc tacctggaac tgaaagaagg cttactggag     1500
ccgctggcag tgacggaacg gctggccatt atctcggtgg taggtgatgg tatgcgcacc     1560
ttgcgtggga tctcggcgaa attctttgcc gcactggccc gcgccaatat caacattgtc     1620
gccattgctc agggatcttc tgaacgctca atctctgtcg tggtaaataa cgatgatgcg     1680
accactggcg tgcgcgttac tcatcagatg ctgttcaata ccgatcaggt tatcgaagtg     1740
tttgtgattg gcgtcggtgg cgttggcggt gcgctgctgg agcaactgaa gcgtcagcaa     1800
agctggctga agaataaaca tatcgactta cgtgtctgcg gtgttgccaa ctcgaaggct     1860
ctgctcacca atgtacatgg ccttaatctg gaaaactggc aggaagaact ggcgcaagcc     1920
aaagagccgt ttaatctcgg gcgcttaatt cgcctcgtga agaatatca tctgctgaac     1980 ccggtcattg ttgactgcac ttccagccag gcagtggcgg atcaatatgc cgacttcctg     2040
cgcgaagg                                                               2048
```

<210> SEQ ID NO 2
<211> LENGTH: 2048
<212> TYPE: DNA
<213> ORGANISM: Escherichia coli

<400> SEQUENCE: 2

```
agcttttcat tctgactgca acgggcaata tgtctctgtg tggattaaaa aaagagtgtc       60
tgatagcagc ttctgaactg gttacctgcc gtgagtaaat taaaatttta ttgacttagg      120
```

```
tcactaaata ctttaaccaa tataggcata gcgcacagac agataaaaat tacagagtac    180
acaacatcca tgaaacgcat tagcaccacc attaccacca ccatcaccat taccacaggt    240
aacggtgcgg gctgacgcgt acaggaaaca cagaaaaaag cccgcacctg acagtgcggg    300
cttttttttt cgaccaaagg taacgaggta acaaccatgc gagtgttgaa gttcggcggt    360
acatcagtgg caaatgcaga acgttttctg cgtgttgccg atattctgga aagcaatgcc    420 aggcagggc aggtggccac cgtcctctct gcccccgcca aaatcaccaa ccacctggtg     480
gcgatgattg aaaaaccat tagcggccag gatgctttac ccaatatcag cgatgccgaa     540 cgtattttg ccgaactttt gacgggactc gccgccgccc agccgggtt cccgctggcg      600 caattgaaaa ctttcgtcga tcaggaattt gcccaaataa acatgtcct gcatggcatt     660 agtttgttgg ggcagtgccc ggatagcatc aacgctgcgc tgatttgccg tggcgagaaa    720
atgtcgatcg ccattatggc cggcgtatta gaagcgcgcg gtcacaacgt tactgttatc    780
gatccggtcg aaaaactgct ggcagtgggg cattacctcg aatctaccgt cgatattgct    840
gagtccaccc ccgtattgc ggcaagccgc attccggctg atcacatggt gctgatggca     900
ggtttcaccg ccggtaatga aaaggcgaa ctggtggtgc ttggacgcaa cggttccgac     960
tactctgctg cggtgctggc tgcctgttta cgcgccgatt gttgcgagat ttggacatta    1020
tggcggccaa cttatacctg cgacccgcgt caggtgcccg atgcgaggtt gttgaagtcg    1080
atgtcctacc aggaagcgat ggagctttcc tacttcggcg ctaaagttct tcaccccgc     1140 accattaccc ccatcgccca gttccagatc ccttgcctga ttaaaaatac cggaaatcct    1200
caagcaccag gtacgctcat tggtgccagc cgtgatgaag acgaattacc ggtcaagggc    1260
atttccaatc tgaataacat ggcaatgttc agcgtttctg gtccggggat gaaagggatg    1320
gtcggcatgg cggcgcgcgt ctttgcagcg atgtcacgcg cccgtatttc cgtggtgctg    1380
attacgcaat catcttccga atacagcatc agtttctgcg ttccacaaag cgactgtgtg    1440
cgagctgaac gggcaatgca ggaagagttc tacctggaac tgaaagaagg cttactggag    1500
ccgctggcag tgacgaacg gctggccatt atctcggtgg taggtgatgg tatgcgcacc    1560
ttgcgtggga tctcggcgaa attctttgcc gcactggccc gcgccaatat caacattgtc    1620
gccattgctc agggatcttc tgaacgctca atctctgtcg tggtaaataa cgatgatgcg    1680
accactggcg tgcgcgttac tcatcagatg ctgttcaata ccgatcaggt tatcgaagtg    1740
tttgtgattg gcgtcggtgg cgttggcggt gcgctgctgg agcaactgaa gcgtcagcaa    1800
agctggctga agaataaaca tatcgactta cgtgtctgcg gtgttgccaa ctcgaaggct    1860
ctgctcacca atgtacatgg ccttaatctg gaaaactggc aggaagaact ggcgcaagcc    1920
aaagagccgt ttaatctcgg gcgcttaatt cgcctcgtga agaatatca tctgctgaac    1980 ccggtcattg ttgactgcac ttccagccag gcagtggcgg atcaatatgc cgacttcctg    2040
cgcgaagg                                                             2048

<210> SEQ ID NO 3
<211> LENGTH: 820
<212> TYPE: PRT
<213> ORGANISM: Escherichia coli

<400> SEQUENCE: 3

Met Arg Val Leu Lys Phe Gly Gly Thr Ser Val Ala Asn Ala Glu Arg
 1               5                  10                  15

Phe Leu Arg Val Ala Asp Ile Leu Glu Ser Asn Ala Arg Gln Gly Gln
```

-continued

```
                20                  25                  30
Val Ala Thr Val Leu Ser Ala Pro Ala Lys Ile Thr Asn His Leu Val
            35                  40                  45
Ala Met Ile Glu Lys Thr Ile Ser Gly Gln Asp Ala Leu Pro Asn Ile
        50                  55                  60
Ser Asp Ala Glu Arg Ile Phe Ala Glu Leu Leu Thr Gly Leu Ala Ala
 65                  70                  75                  80
Ala Gln Pro Gly Phe Pro Leu Ala Gln Leu Lys Thr Phe Val Asp Gln
                    85                  90                  95
Glu Phe Ala Gln Ile Lys His Val Leu His Gly Ile Ser Leu Leu Gly
                100                 105                 110
Gln Cys Pro Asp Ser Ile Asn Ala Ala Leu Ile Cys Arg Gly Glu Lys
            115                 120                 125
Met Ser Ile Ala Ile Met Ala Gly Val Leu Glu Ala Arg Gly His Asn
    130                 135                 140
Val Thr Val Ile Asp Pro Val Glu Lys Leu Leu Ala Val Gly His Tyr
145                 150                 155                 160
Leu Glu Ser Thr Val Asp Ile Ala Glu Ser Thr Arg Arg Ile Ala Ala
                165                 170                 175
Ser Arg Ile Pro Ala Asp His Met Val Leu Met Ala Gly Phe Thr Ala
            180                 185                 190
Gly Asn Glu Lys Gly Glu Leu Val Val Leu Gly Arg Asn Gly Ser Asp
        195                 200                 205
Tyr Ser Ala Ala Val Leu Ala Ala Cys Leu Arg Ala Asp Cys Cys Glu
    210                 215                 220
Ile Trp Thr Asp Val Asp Gly Val Tyr Thr Cys Asp Pro Arg Gln Val
225                 230                 235                 240
Pro Asp Ala Arg Leu Leu Lys Ser Met Ser Tyr Gln Glu Ala Met Glu
                245                 250                 255
Leu Ser Tyr Phe Gly Ala Lys Val Leu His Pro Arg Thr Ile Thr Pro
            260                 265                 270
Ile Ala Gln Phe Gln Ile Pro Cys Leu Ile Lys Asn Thr Gly Asn Pro
        275                 280                 285
Gln Ala Pro Gly Thr Leu Ile Gly Ala Ser Arg Asp Glu Asp Glu Leu
    290                 295                 300
Pro Val Lys Gly Ile Ser Asn Leu Asn Asn Met Ala Met Phe Ser Val
305                 310                 315                 320
Ser Gly Pro Gly Met Lys Gly Met Val Gly Met Ala Ala Arg Val Phe
                325                 330                 335
Ala Ala Met Ser Arg Ala Arg Ile Ser Val Val Leu Ile Thr Gln Ser
            340                 345                 350
Ser Ser Glu Tyr Ser Ile Ser Phe Cys Val Pro Gln Ser Asp Cys Val
        355                 360                 365
Arg Ala Glu Arg Ala Met Gln Glu Glu Phe Tyr Leu Glu Leu Lys Glu
    370                 375                 380
Gly Leu Leu Glu Pro Leu Ala Val Thr Glu Arg Leu Ala Ile Ile Ser
385                 390                 395                 400
Val Val Gly Asp Gly Met Arg Thr Leu Arg Gly Ile Ser Ala Lys Phe
                405                 410                 415
Phe Ala Ala Leu Ala Arg Ala Asn Ile Asn Ile Val Ala Ile Ala Gln
            420                 425                 430
Gly Ser Ser Glu Arg Ser Ile Ser Val Val Val Asn Asn Asp Asp Ala
        435                 440                 445
```

```
Thr Thr Gly Val Arg Val Thr His Gln Met Leu Phe Asn Thr Asp Gln
    450                 455                 460

Val Ile Glu Val Phe Val Ile Gly Val Gly Val Gly Gly Ala Leu
465             470                 475                 480

Leu Glu Gln Leu Lys Arg Gln Gln Ser Trp Leu Lys Asn Lys His Ile
                485                 490                 495

Asp Leu Arg Val Cys Gly Val Ala Asn Ser Lys Ala Leu Leu Thr Asn
                500                 505                 510

Val His Gly Leu Asn Leu Glu Asn Trp Gln Glu Leu Ala Gln Ala
515                 520                 525

Lys Glu Pro Phe Asn Leu Gly Arg Leu Ile Arg Leu Val Lys Glu Tyr
    530                 535                 540

His Leu Leu Asn Pro Val Ile Val Asp Cys Thr Ser Ser Gln Ala Val
545                 550                 555                 560

Ala Asp Gln Tyr Ala Asp Phe Leu Arg Glu Gly Phe His Val Val Thr
                565                 570                 575

Pro Asn Lys Lys Ala Asn Thr Ser Ser Met Asp Tyr Tyr His Gln Leu
                580                 585                 590

Arg Tyr Ala Ala Glu Lys Ser Arg Arg Lys Phe Leu Tyr Asp Thr Asn
    595                 600                 605

Val Gly Ala Gly Leu Pro Val Ile Glu Asn Leu Gln Asn Leu Leu Asn
    610                 615                 620

Ala Gly Asp Glu Leu Met Lys Phe Ser Gly Ile Leu Ser Gly Ser Leu
625                 630                 635                 640

Ser Tyr Ile Phe Gly Lys Leu Asp Glu Gly Met Ser Phe Ser Glu Ala
                645                 650                 655

Thr Thr Leu Ala Arg Glu Met Gly Tyr Thr Glu Pro Asp Pro Arg Asp
                660                 665                 670

Asp Leu Ser Gly Met Asp Val Ala Arg Lys Leu Leu Ile Leu Ala Arg
    675                 680                 685

Glu Thr Gly Arg Glu Leu Glu Leu Ala Asp Ile Glu Ile Glu Pro Val
    690                 695                 700

Leu Pro Ala Glu Phe Asn Ala Glu Gly Asp Val Ala Ala Phe Met Ala
705                 710                 715                 720

Asn Leu Ser Gln Leu Asp Asp Leu Phe Ala Ala Arg Val Ala Lys Ala
                725                 730                 735

Arg Asp Glu Gly Lys Val Leu Arg Tyr Val Gly Asn Ile Asp Glu Asp
                740                 745                 750

Gly Val Cys Arg Val Lys Ile Ala Glu Val Asp Gly Asn Asp Pro Leu
            755                 760                 765

Phe Lys Val Lys Asn Gly Glu Asn Ala Leu Ala Phe Tyr Ser His Tyr
    770                 775                 780

Tyr Gln Pro Leu Pro Leu Val Leu Arg Gly Tyr Gly Ala Gly Asn Asp
785                 790                 795                 800

Val Thr Ala Ala Gly Val Phe Ala Asp Leu Leu Arg Thr Leu Ser Trp
                805                 810                 815

Lys Leu Gly Val
            820
```